US012465737B2

(12) United States Patent
Bennett et al.

(10) Patent No.: US 12,465,737 B2
(45) Date of Patent: Nov. 11, 2025

(54) PILL WITH NEEDLE DELIVERY SYSTEM HAVING OUTWARDLY EXPANDING MECHANICAL ACTUATION

(71) Applicant: Verily Life Sciences LLC, South San Francisco, CA (US)

(72) Inventors: Eric Bennett, San Carlos, CA (US); Kimberly Kam, Orinda, CA (US); Martin Sheridan, Redwood City, CA (US); Annapurna Karicherla, Cupertino, CA (US); Kassidy MacPhail, San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 1148 days.

(21) Appl. No.: 17/381,861

(22) Filed: Jul. 21, 2021

(65) Prior Publication Data

US 2022/0032028 A1 Feb. 3, 2022

Related U.S. Application Data

(60) Provisional application No. 63/058,842, filed on Jul. 30, 2020.

(51) Int. Cl.
*A61M 37/00* (2006.01)
*A61M 31/00* (2006.01)

(52) U.S. Cl.
CPC ...... *A61M 37/0015* (2013.01); *A61M 31/002* (2013.01); *A61M 2037/0023* (2013.01);
(Continued)

(58) Field of Classification Search
CPC ...... A61M 37/0015; A61M 2037/0023; A61M 31/002; A61M 2037/0061; A61M 5/2033;
(Continued)

(56) References Cited

U.S. PATENT DOCUMENTS 4,239,040 A 12/1980 Hosoya et al.
5,443,843 A 8/1995 Curatolo et al.
(Continued)

FOREIGN PATENT DOCUMENTS

CA 3117947 5/2020
EP 1980290 2/2013
(Continued)

OTHER PUBLICATIONS

PCT/US2021/042551 , "Invitation to Pay Additional Fees and, Where Applicable, Protest Fee", Nov. 18, 2021, 16 pages.
(Continued)

*Primary Examiner* — Wesley G Harris
(74) *Attorney, Agent, or Firm* — Kilpatrick Townsend & Stockton LLP

(57) ABSTRACT

A device can include a capsule containing an array of microneedles and a mechanical actuator. The device can be in an ingestible form for delivery to a duodenum or other target location within a subject and can release the mechanical actuator from constraint by the capsule in response to stimuli or conditions in or en route to the duodenum or other target location. The mechanical actuator upon release from constraint by the capsule can expand outwardly (e.g., responsive to a bias provided by a flexibly resilient material of the mechanical actuator) in a direction away from a central longitudinal axis of the mechanical actuator and drive the array of microneedles into penetrating engagement with a lining of the duodenum or other target location. The penetrating engagement can facilitate delivery of a biotherapeutic agent or other payload via the microneedles.

18 Claims, 16 Drawing Sheets

(52) U.S. Cl.
CPC ............... *A61M 2037/0046* (2013.01); *A61M 2205/0266* (2013.01); *A61M 2210/1057* (2013.01)

(58) Field of Classification Search
CPC .. A61M 2037/0046; A61M 2205/0266; A61M 2210/1057; A61M 2210/1042; A61M 2210/1053; A61M 2210/106; A61M 2210/1064; A61M 2025/1086; A61M 2025/105; A61M 31/00; A61M 2205/04; A61K 9/0021; A61K 9/48; C12N 2310/20; A61F 2/2454; A61F 2/246; A61F 2/243; A61F 2/95; A61B 5/07; A61B 5/073; A61B 5/076; A61B 5/145; A61B 5/1477; A61B 5/14514
See application file for complete search history.

(56) References Cited

U.S. PATENT DOCUMENTS

| | | | | |
|---|---|---|---|---|
| 8,734,429 | B2 | 5/2014 | Imran et al. | |
| 9,149,617 | B2 | 10/2015 | Imran | |
| 10,046,109 | B2 | 8/2018 | Zou et al. | |
| 2005/0187530 | A1 | 8/2005 | Davidson et al. | |
| 2009/0240270 | A1* | 9/2009 | Schneider | A61B 17/320725 606/198 |
| 2010/0063486 | A1 | 3/2010 | Dijksman et al. | |
| 2011/0087195 | A1 | 4/2011 | Uhland et al. | |
| 2011/0160699 | A1* | 6/2011 | Imran | A61K 38/29 604/93.01 |
| 2012/0165796 | A1 | 6/2012 | Ortiz et al. | |
| 2013/0165372 | A1* | 6/2013 | Imran | A61K 38/26 604/174 |
| 2013/0165772 | A1 | 6/2013 | Traverso et al. | |
| 2013/0165859 | A1* | 6/2013 | Imran | A61M 31/002 604/93.01 |
| 2015/0064241 | A1 | 3/2015 | Conrad | |
| 2015/0119879 | A1 | 4/2015 | Jameson et al. | |
| 2016/0015648 | A1 | 1/2016 | Gross et al. | |
| 2017/0174758 | A1 | 6/2017 | Imran | |
| 2017/0231902 | A1 | 8/2017 | Imran | |
| 2020/0054568 | A1 | 2/2020 | Gross et al. | |
| 2022/0257855 | A1* | 8/2022 | Traverso | A61K 9/0012 |

FOREIGN PATENT DOCUMENTS

| | | | | |
|---|---|---|---|---|
| JP | 2016-529066 A | | 9/2016 | |
| NO | 178426 | | 12/1995 | |
| WO | WO-9702859 A1 | * | 1/1997 | A61M 25/0084 |
| WO | 2011017023 | | 2/2011 | |
| WO | 2020102650 | | 5/2020 | |
| WO | WO-2020101737 A1 | * | 5/2020 | A61M 31/00 |
| WO | WO-2020102650 A2 | * | 5/2020 | A61M 31/002 |

OTHER PUBLICATIONS

International Application No. PCT/US2021/042551 , International Search Report and Written Opinion, Mailed On Mar. 10, 2022, 26 pages.

Fox et al., "Micro/nanofabricated Platforms for Oral Drug Delivery", J Control Release, vol. 219, 2015, p. 431.

Traverso et al., "Microneedles for Drug Delivery via the Gastrointestinal Tract", J Pharma Sci, vol. 104, 2015, p. 362.

Japan Appl. No. 2022-577771, Notice of Reasons for Refusal, dated May 20, 2025.

* cited by examiner

PILL WITH NEEDLE DELIVERY SYSTEM HAVING OUTWARDLY EXPANDING MECHANICAL ACTUATION

CROSS-REFERENCE TO RELATED APPLICATIONS

The present application claims the benefit of U.S. Provisional Patent Application 63/058,842, filed Jul. 30, 2020, the entirety of which is hereby incorporated by reference.

TECHNICAL FIELD

The present disclosure generally relates to systems for delivering drugs or other payloads inside the body of a subject and, more specifically, but not necessarily limited to, ingestible pills containing needle delivery systems that are actuatable to deliver a payload to some portion of a lining of a gastrointestinal tract of the subject.

BACKGROUND

Various compounds, such as biotherapeutics (e.g., including peptides, proteins, antibodies, and nucleic acids), traditionally have been ineffective to deliver orally because they are at least 100 times in magnitude too large compared to recognized size limits for orally deliverable drugs. For example, where a biotherapeutic may be approximately 150 kilodaltons (kDa) in size, an orally deliverable drug may be approximately 0.5 kDa in size. In comparison to traditional small molecule therapeutics that can be orally delivered and absorbed during the process of digestion, biotherapeutics often bring better efficacy and specificity but at the cost of drug delivery challenges. In essence, the large size of these biotherapeutic drugs has conventionally necessitated frequent delivery through needle injections, such as through a handheld syringe or an intravenous catheter commonly referred to as an IV. However, injections or infusions may contribute to patient compliance challenges, high administration costs by trained medical staff, needlestick contamination, needle phobia, and a heightened risk of systemic infection.

SUMMARY

Various examples of the present disclosure are directed to pills or capsules that contain compact needle delivery systems that utilize outwardly expanding mechanical actuation to drive needles into engagement with a lining of a gastrointestinal tract or other body lumen, e.g., to facilitate delivery of therapeutic agents or other payloads through such engagement inside the body of a subject.

In one example, a system includes a capsule. The capsule includes a shell having an inner surface defining an interior volume of the capsule. The shell also has an outer surface sized to pass through a lumen defined by a lining of a gastrointestinal tract. The system can also include a carrier sized to fit within the interior volume of the capsule and bearing an array of microneedles. In addition, the system also includes a mechanical actuator operable for moving the carrier outwardly to cause the microneedles to penetrate the lining of the gastrointestinal tract. The mechanical actuator includes a foldable biasing member, which includes a first end and a second end. The foldable biasing member includes a flexibly resilient material having a flexibility permitting the first end and the second end to be foldable toward one another for movement from an expanded state toward a collapsed state in which the mechanical actuator fits within the interior volume of the capsule. The flexibly resilient material further can have a resiliency that biases the first end and the second end apart from one another for movement from the collapsed state toward the expanded state to move the carrier outwardly upon the mechanical actuator overcoming or escaping from constraint provided by the capsule. The mechanical actuator can also include a holder hingedly attached with the first end of the biasing member. The holder can include a support surface for supporting the carrier bearing the array of microneedles.

In another example, a system includes a capsule. The capsule includes a shell having a first shell portion, a second shell portion, and a joint releasably attaching the first shell portion with the second shell portion. The capsule also includes an inner surface defined at least in part by the first shell portion and the second shell portion and defining an interior volume of the capsule. In addition, the capsule includes an outer surface defined at least in part by the first shell portion and the second shell portion and sized to pass through a lumen defined by a lining of a gastrointestinal tract. The system can also include a carrier sized to fit within the interior volume of the capsule and bearing an array of microneedles. In addition, the system can include a launcher operable upon overcoming or escaping from constraint provided by the joint and operable for driving the first shell portion and the second shell portion away from the carrier to expose the array of microneedles.

In a further example, a system includes a mechanical actuator configured for microneedle delivery. The mechanical actuator includes a foldable biasing member comprising a first end and a second end. The foldable biasing member can include a flexibly resilient material having a flexibility permitting the first end and the second end to be foldable toward one another for movement from an expanded state toward a collapsed state in which the mechanical actuator fits within a volume sized to fit within an ingestible capsule. The flexibly resilient material further can have a resiliency that biases the first end and the second end apart from one another for movement from the collapsed state toward the expanded state. The mechanical actuator also can include a holder hingedly attached with the first end of the biasing member. The holder can include a support surface configured for supporting a carrier bearing an array of microneedles. The support surface can be configured for supporting the carrier for outward movement for deployment of the microneedles in response to movement from the collapsed state toward the expanded state.

In yet another example, a device includes a capsule containing an array of microneedles and a launcher. The device is in an ingestible form for delivery to a duodenum of a subject and releases a first shell portion and a second shell portion of the capsule from one another in response to stimuli or conditions in or en route to the duodenum. The launcher drives the released first shell portion and the second shell portion away from one another to expose the array of microneedles in a position for achieving penetrating engagement with a lining of the duodenum caused by peristaltic contraction of the lining of the duodenum about the exposed array of microneedles. The penetrating engagement facilitates delivery of a payload via the microneedles.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
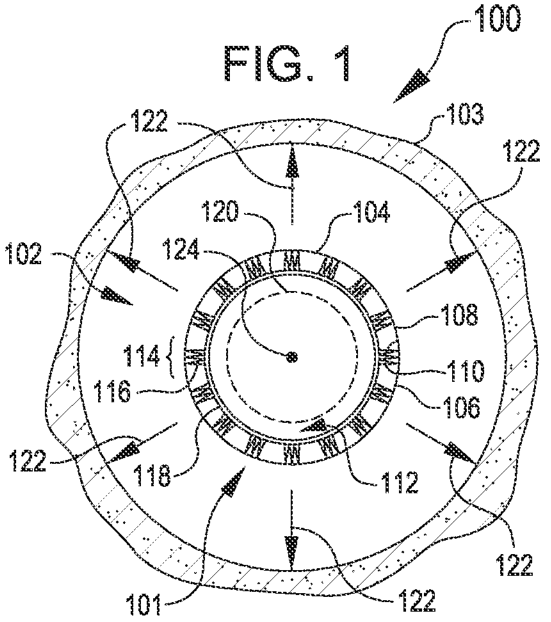
FIG. 1 shows an end view of a collapsed, ready state of a system for delivery of a therapeutic agent or other payload within a body according to certain examples of the present disclosure.

Examples are described herein in the context of pills or capsules that contain compact needle delivery systems. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a subject may wish to take a dose of a biotherapeutic agent or other compound without resorting to a syringe injection, intravenous infusion, and potential accompanying discomfort or other concerns. To this end, the person may use a device according to this disclosure to provide the dosage. In this example, the device may be provided in pill or capsule form that the subject can swallow. Inside the pill or capsule are components capable of deploying within the body to effectively provide an internal injection, which may cause much smaller tissue disturbances and fewer systemic effects as compared to an external injection or infusion. As the pill or capsule reaches a target portion of the gastrointestinal tract (such as the duodenum), a specialized coating of the pill or capsule has dissolved or degraded sufficiently to break apart and allow a mechanical actuator within the pill to expand outwardly. Various options may be employed for the outwardly expanding mechanical actuators, such as a normally- or radially-expanding stent-like tube, an unwinding coil, an unfurling set of curved arms, a set of double-hinged arms that unfold relative to a central hub and then unfold again relative to parts connected to the hub, or a scissor-lift-like arrangement with centrally-hinged lateral columns that pop upright to an expanded state from a compressed state in which portions of the columns are hinged toward each other. Multiple arrays of microneedles are arranged about the mechanical actuator and are driven by the outward expansion into engagement with surrounding tissue (e.g., tissue of a mucosal lining of the duodenum). The drug dose can be delivered to the tissue through the engaged microneedles, such as by flowing through the microneedles if hollow or by direct absorption if the drug is embedded in a dissolvable composition of the microneedles. After delivery of the dosage, the constituent parts of the device may biodegrade and avoid possible complications from trying to pass the device remains out of the body. Thus, the subject may use the device to administer an internal injection that may ultimately be less invasive, less arduous, and/or less troublesome to the subject than the alternative of using an external syringe or intravenous infusion.

Figure 2:
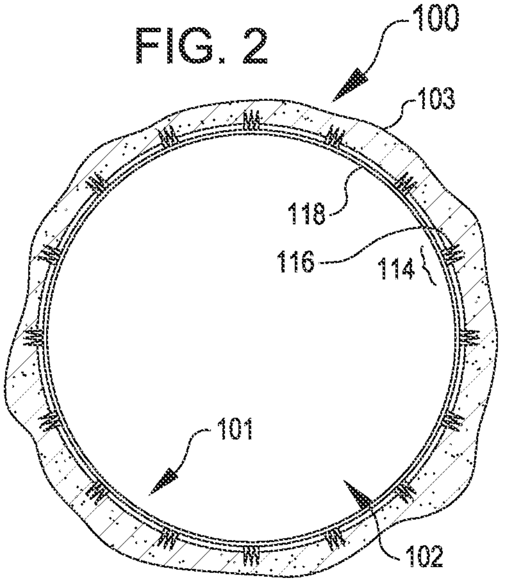
FIG. 2 shows an end view of an expanded, deployed state of the system of FIG. 1 according to certain examples of the present disclosure.

Turning now to the drawings (which are rendered for purposes of illustrating principles and thus may not necessarily be to scale), FIGS. 1 and 2 illustrate different states of a system 100 for delivery of a drug or other payload within a body. The system 100 may include a device 101 that can be situated within a body lumen 102, e.g., which may be surrounded or otherwise at least partially bounded by a lumen wall 103 formed of tissue lining the lumen 102. The device 101 can include or fit within a capsule 104. Generally, the capsule 104 can provide a constraint (e.g., as depicted in FIG. 1) that can be overcome, escaped, or otherwise eliminated (e.g., as depicted in FIG. 2) at a target location within a subject to permit the device 101 to expand outwardly and engage tissue at the target location for delivery of a drug or other payload. In various examples, the device 101 may allow payload delivery without significant blockage of the body lumen 102 and/or without substantial shearing forces on the mucosal lining or other lining or lumen wall 103 of the body lumen 102. In some examples, the device 101 may be constructed entirely of biodegradable materials and allow the device 101 to be fully biodegradable. The device 101 being biodegradable may allow the device 101 after use to be absorbed by the body of the subject instead of leaving some portion that requires passing via excretion to be eliminated from the subject, although in some instances, at least a portion of broken-down biodegradable material of the device 101 may be eliminated via excretion.

The capsule 104 (e.g., FIG. 1) can include a shell 106. The shell 106 can include or be supplemented with one or more layers of like or different compositions to provide variations in functions, such as impacting where in the subject the capsule 104 may degrade or otherwise release the device 101 from constraint by the capsule. The shell 106 can have or define an outer surface 108 and an inner surface 110.

The outer surface 108 of the capsule 104 can be sized to pass through the body lumen 102. For example, the body lumen 102 may correspond to a lumen having a lumen wall 103 defined by a lining of a gastrointestinal tract. In some examples, the capsule 104 can meet criteria for being classified as a 000 capsule as known by persons of skill in the art, although other standardized or custom types of capsule 104 may be used. The capsule 104 may be sized to facilitate functioning in a particular body portion. For example, a capsule 104 of 000 type may have an outer surface 108 with an overall length of approximately 26.14 mm (millimeters) in length and a body diameter of 9.55 mm, which dimensions may be suitable for operation or use in a portion of the gastrointestinal tract corresponding to the duodenum (e.g., based on a human duodenum typically ranging from between 25 mm when fully open and nearly 0 mm when fully closed or constricted during peristalsis). In some examples, a length of the capsule 104 being greater than or approximately equal to a largest expected diameter or other cross-sectional dimension of the body lumen 102 may pre-dispose the capsule toward a pre-determined orientation in which the device 101 is suitably aligned for expanding to engage with the surrounding tissue of the lumen wall 103 (e.g., with lengths of the capsule 104 and body lumen 102 aligned so the device 101 can expand along diameters of the device 101 and body lumen 102).

The inner surface 110 can bound or otherwise define an interior volume 112 of the capsule 104, e.g., in which the device 101 and/or respective components may be disposed. The inner surface 110 may be separated from the outer surface 108 by a wall thickness, e.g., such that dimensions between respective portions of the inner surface 110 may be reduced by two times the wall thickness from dimensions of the outer surface 108. As an illustrative example, a capsule 104 of 000 type may have a wall thickness of 0.11 mm such that the interior volume 112 has overall internal length of approximately 25.92 mm (millimeters) and an internal body diameter of 9.33 mm.

FIG. 1 depicts various components of the device 101 within the capsule 104. For example, the device 101 can include at least one array 114 of microneedles 116, a carrier 118, and a mechanical actuator 120. The array 114 can be borne by the carrier 118. In use, the mechanical actuator 120 may be capable of moving the carrier 118. For example, the mechanical actuator 120 may move the carrier 118 outward, such as illustrated by arrows 122. The outward movement may correspond to movement away from a central axis 124 of the mechanical actuator 120. (For example, the central axis 124 in FIG. 1 is depicted as a dot representing an axis aligned in a direction traveling into or out of the page in the view of FIG. 1.) The outward movement of the carrier 118 caused by the mechanical actuator 120 can result in movement of the microneedles 116 toward or into engagement with tissue of the lumen wall 103 of the body lumen 102, such as from the position depicted in FIG. 1 and toward or into the position depicted in FIG. 2.

The microneedles 116 may correspond to any suitable from of tissue-penetrating members capable of providing a payload to associated tissue. In some examples, the microneedles 116 include a dissolvable composition that contains the payload, e.g., such that the payload may be absorbed into engaged tissue as the engaged microneedles dissolve. Additionally or alternatively, the microneedles 116 may be hollow or otherwise include passages through which the payload can flow for delivery.

The microneedles 116 may be suitably sized and arranged for their function. For example, the microneedles 116 may be "micro" in the sense that the microneedles may be sufficiently small to fit within the capsule 104 with other components of the device 101. In an illustrative example, the microneedles 116 may have a length of approximately 1.5 mm such that provision of microneedles 116 on opposite sides within a capsule 104 would occupy approximately 3 mm of a diameter of the capsule 104, e.g., leaving approximately 6.33 mm of the 9.33 mm internal diameter available for other components in a capsule 104 of a 000 type.

The microneedles 116 may be distributed in any suitable manner. In some examples, the microneedles 116 are grouped in arrays 114 that are in turn distributed relative to one another. For example, FIG. 1 depicts sixteen arrays 114 equally distributed around a circumference, although any other number of one or more arrays 114 could be utilized and can be distributed evenly or unevenly. Generally, arrays 114 utilized may include any number of one or more columns and/or one or more rows of microneedles 116 (or any other cluster or arrangement that may be staggered or otherwise not clearly defined in terms of columns or rows). For example, although FIG. 1 depicts an arrangement of sixteen arrays 114 in which each has three columns and a single row visible, another illustrative arrangement could have six arrays 114 each having two columns and twelve rows, or any other suitable combination of number of arrays, columns, and rows could be utilized. Furthermore, although a single microneedle 116 could be utilized for the device 101 or within a respective array 114, amounts of payload that can be delivered may be increased by increasing the number of microneedles 116 included.

In some examples, the microneedles 116 and/or arrays 114 may additionally or alternatively include particular geometry or other particular physical features (such as sharpness and/or pitch) that can facilitate piercing or other engagement with respective lining of the lumen wall 103 of the body lumen 102. Some examples of such features are described further herein with respect to FIG. 17.

The carrier 118 is depicted in FIG. 1 as a band that is expandable in a normal or radial direction under the influence of the mechanical actuator 120. However, the carrier 118 is not limited to a form factor of a band. The carrier 118 may correspond to any suitable structure for supporting the microneedles 116.

The carrier 118 may interact in any suitable fashion with the mechanical actuator 120 to move the microneedles 116 outward. In some examples, the carrier 118 and the mechanical actuator 120 may correspond to distinct structures. For example, in FIG. 1, the carrier 118 is depicted as separate from and positioned around the mechanical actuator 120, e.g., such that the mechanical actuator 120 may begin at least partially out of contact with the carrier 118 and expand outwardly to come into contact with the carrier 118 to drive the carrier 118 outwardly along with the microneedles 116 borne by the carrier 118. The carrier 118 may alternatively begin at least partially in contact with the mechanical actuator 120. In some examples, the carrier 118 and the mechanical actuator 120 are coupled together to remain in contact regardless of whether the mechanical actuator 120 is expanded or collapsed. In some examples, the carrier 118 may be a subcomponent of the mechanical actuator 120 or vice versa. For example, the carrier 118 may be integrally formed in—or otherwise correspond to—a portion of the mechanical actuator 120.

Any suitable mechanical actuator 120 may be used to move the carrier 118. To this end, the mechanical actuator 120 is depicted in FIG. 1 in generalized terms as a functional block represented by a dashed line (and omitted from view for clarity in FIG. 2). Various examples of suitable mechanical actuators 120 are depicted and/or described with reference to other figures herein, and any of these mechanical actuators 120 could be utilized in conjunction with the arrangement depicted and/or described with respect to FIG. 1, such as by substitution into the place shown by the dashed line denoting the mechanical actuator 120 in FIG. 1. For example, the mechanical actuators 120 of other figures herein may be provided without the directly mounted microneedles 116 shown in those figures for greater ease of incorporating into the arrangement depicted and/or described with reference to FIG. 1, e.g., such that microneedles 116 are provided on the carrier 118 without a separate set being incorporated into or onto the mechanical actuator 120.

In some examples, the carrier 118 being a band may permit microneedles 116 to be moved directly outward in a radial or normal direction (which may correspond to a direction perpendicular to the long axis of the lumen 102) regardless of whether the mechanical actuator 120 expands directly in a radial or normal direction. For example, the carrier 118 being a band may effectively constrain the microneedles 116 to move directly radially/normally and/or convert or nullify non-radial or non-normal components of motion from the mechanical actuator 120.

The mechanical actuator 120 can include suitable structure to provide outward expansion for moving the carrier 118. The structure can include or be coupled with suitable material for providing the outward expansion. For example, the mechanical actuator 120 can include a flexibly resilient material. The material can have or exhibit a flexibility that permits collapsing of the mechanical actuator 120 (e.g., away from an expanded state as in FIG. 2 and/or toward a collapsed state as in FIG. 1). The collapsing may allow the mechanical actuator 120 to fit within the interior volume 112 of the capsule. The material can additionally have or exhibit a resiliency that biases the mechanical actuator 120 toward outward expansion (e.g., away from the state shown in FIG. 1 to that shown in FIG. 2 or otherwise away from the collapsed state and toward the expanded state). The outward expansion may move the carrier 118 outwardly upon the mechanical actuator 120 overcoming or escaping from constraint provided by the capsule 104.

Any suitable technique may be utilized to facilitate the mechanical actuator 120 overcoming or escaping from constraint provided by the capsule 104. In some examples, the capsule 104 may break down or degrade at a particular target location within the subject and permit the constraint to be overcome. For example, the shell 106 of the capsule 104 may include a suitable composition and/or thickness of enteric coating to permit degradation at a target location. The resiliency of the material of the mechanical actuator 120 may aid in the breakdown of the capsule 104. For example, the capsule 104 may degrade to a certain thickness or strength that can be overcome by force provided by the pre-loaded mechanical actuator 120. In some examples, the capsule 104 may contain components to launch or eject the mechanical actuator 120, e.g., which may be in addition to or as an alternative to releasing the constraint by degradation of the capsule 104. Generally, any suitable technique may be utilized to trigger release or elimination of the constraint from the mechanical actuator 120, including but not limited to, construction of the capsule 104 in part or in whole of coatings or other materials that may cause release in response to stimuli or conditions in or en route to the duodenum or other target location. For example, release may be triggered in response to a chemical (such as pH), electrical, mechanical, or external stimulus (such as ultrasound energy that may be applied to affect particular compositions). Once freed from the constraint provided by the capsule 104, the mechanical actuator 120 may provide adequate velocity and/or force to drive the microneedles 116 into engagement with the tissue of the lumen wall 103 of the body lumen 102 (such as to a position depicted in FIG. 2) for delivery of the payload.

Figure 3:
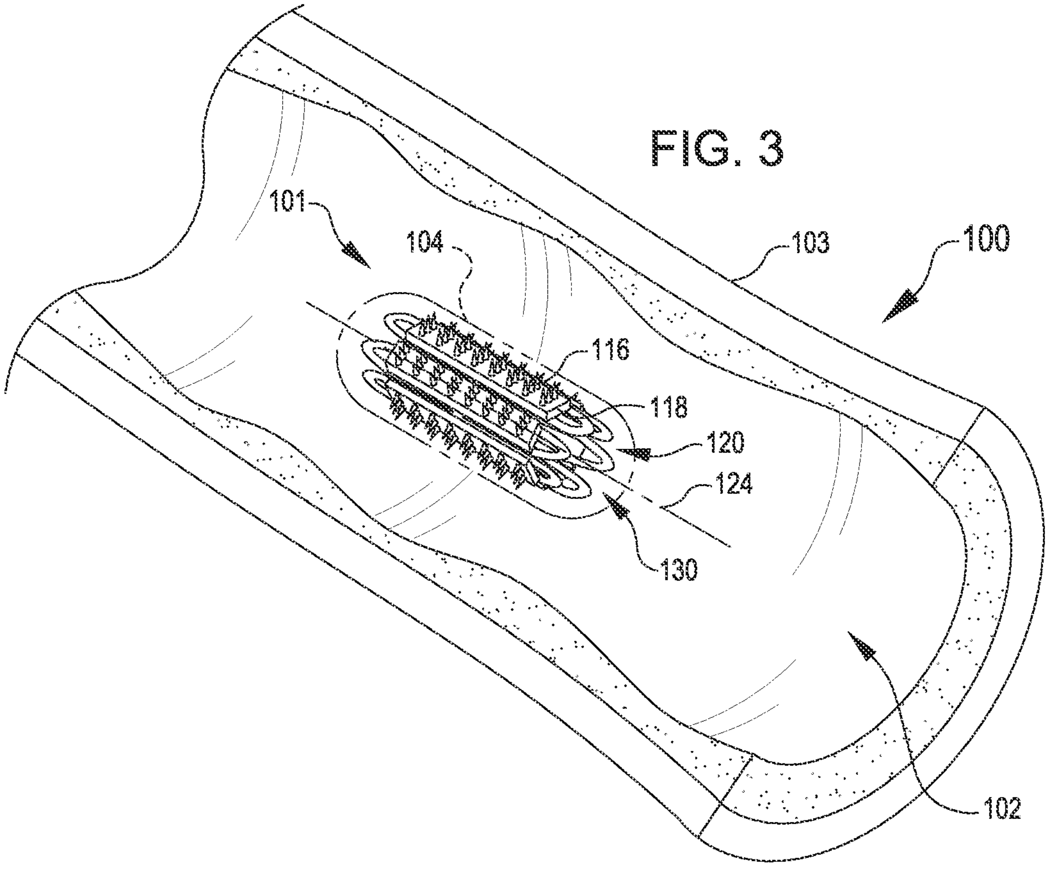
FIG. 3 shows a perspective view of a collapsed, ready state of a tubular actuator that may be utilized with the system of FIG. 1 according to certain examples of the present disclosure.
Figure 5:
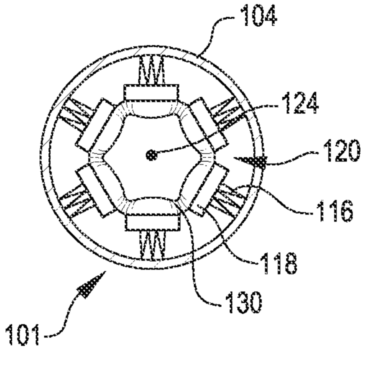
FIG. 5 shows an end view of the collapsed, ready state of the tubular actuator of FIGS. 3-4 according to certain examples of the present disclosure.
Figure 6:
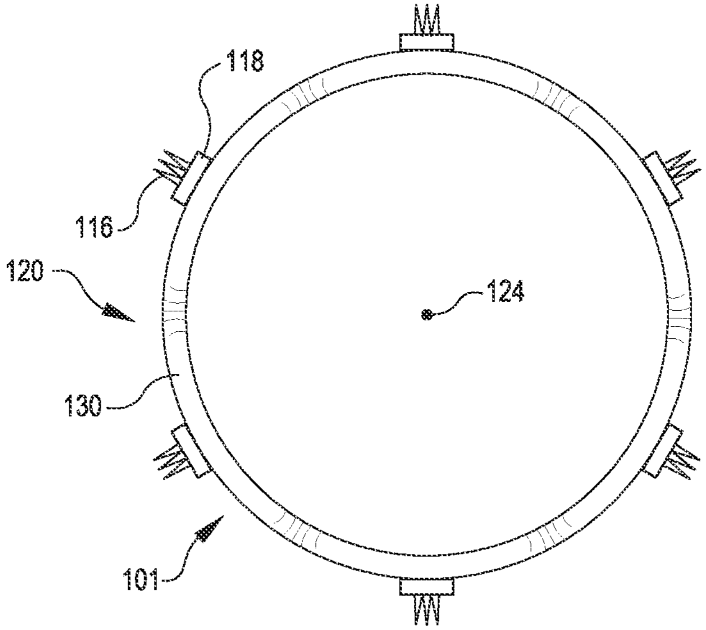
FIG. 6 shows an end view of the expanded, deployed state of the tubular actuator of FIGS. 3-5 according to certain examples of the present disclosure.

FIG. 3 is a perspective view showing further examples of structure that may be incorporated into the system 100. In some examples (such as in FIG. 3), the mechanical actuator 120 may include a collapsible tube 130. The collapsible tube 130 may be compressible toward and expandable away from the central longitudinal axis 124 of the mechanical actuator 120 (e.g., in a radial or normal direction, which may correspond to a direction perpendicular to the long axis of the lumen 102). For example, where FIGS. 3 and 5 respectively show perspective and end views of the collapsible tube 130 in a ready, collapsed state, FIGS. 4 and 6 respectively show perspective and end views of the collapsible tube 130 in an expanded, deployed state.

Microneedles 116 are depicted as supported by carriers 118 that are separately mounted to the collapsible tube 130, although other arrangements are possible, including, but not limited to arrangements in which the microneedles 116 and/or carriers 118 are instead integrally formed, or arrangements in which the carrier 118 corresponds to a band or other distinct structure such as described with respect to FIGS. 1 and 2.

Figure 4:
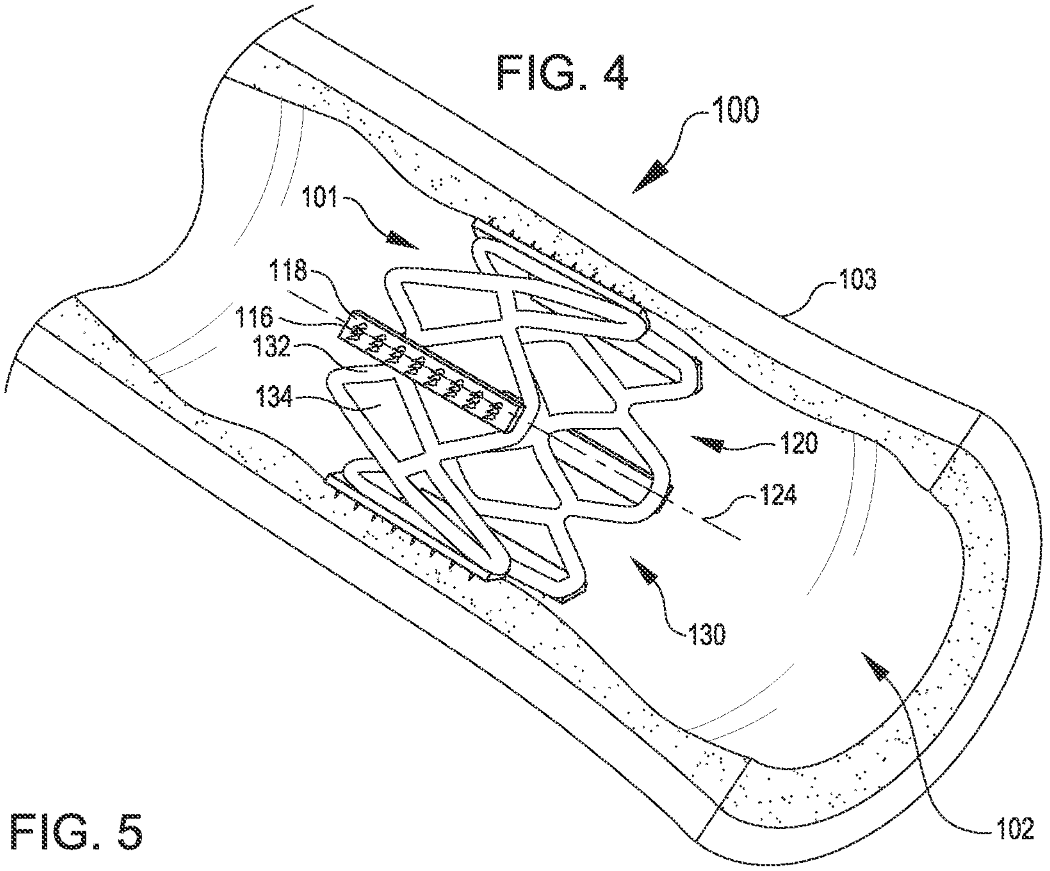
FIG. 4 shows a perspective view of an expanded, deployed state of the tubular actuator of FIG. 3 according to certain examples of the present disclosure.

As may be best seen in FIG. 4, the collapsible tube 130 may be formed of a network of interconnected flexible members 132. The members 132 may be arranged in a lattice or lacing form. Spacing between the members 132 may be greater in the expanded state than in the collapsed state. For example, windows 134 may be formed in between respective members 132, and each window 134 may represent a smaller cross-sectional opening in the collapsed state compared to the expanded state. In some examples, the members 132 and/or windows 134 may compress along a periphery of the collapsible tube 130. For example, the members 132 may compress into spaces defined by the windows 134. In some examples, (such as may be best seen in comparing FIGS. 5 and 6), the tube 130 when compressed may appear as having a smaller periphery than when expanded, e.g., rather than folding in a manner that causes portions to jut inward from the periphery of the collapsible tube 130. In some examples, an overall length of the collapsible tube is substantially the same in both the expanded and collapsed states.

The members 132 may be formed of a flexibly resilient material. For example, the material may provide sufficient flexibility to allow the collapsible tube 130 to compress from the expanded state toward the compressed state, and the material may also provide sufficient resiliency to bias the material toward expanding away from the compressed state and toward the expanded state, e.g., to drive microneedles 116 outward for tissue engagement. In some examples, the members 132 are constructed of biodegradable material (e.g., capable of degrading within a gastrointestinal tract or a within a particular target portion thereof). In some examples, the members 132 are constructed of material suitable for constructing the collapsible tube 130 by 3D-printing (three-dimensional printing) or other specific fabrication techniques. Some suitable examples of materials for the members 132 can include stereolithography (SLA) 3D-printed durable resin, gelatin paper or sheets, rice paper or sheets, polylactic acid, nylon, polyester, PVA (polyvinyl alcohol), or corn-based polymers.

In use, the collapsible tube 130 may provide a central and substantial through-passage in the expanded state and thus prevent or avoid full obstruction or occlusion of the lumen of the duodenum or other relevant body lumen 102. Additionally, the collapsible tube 130 may provide a normally outward or radially outward movement of the microneedles 116 into the lining of the lumen wall 103 of the body lumen 102, e.g., in a direction perpendicular to the long axis of the lumen so as to reduce or avoid shearing forces that might occur if the mechanical actuator 120 instead imparted some tangentially-oriented components in addition to radially-oriented or perpendicularly-oriented components.

Figure 7:
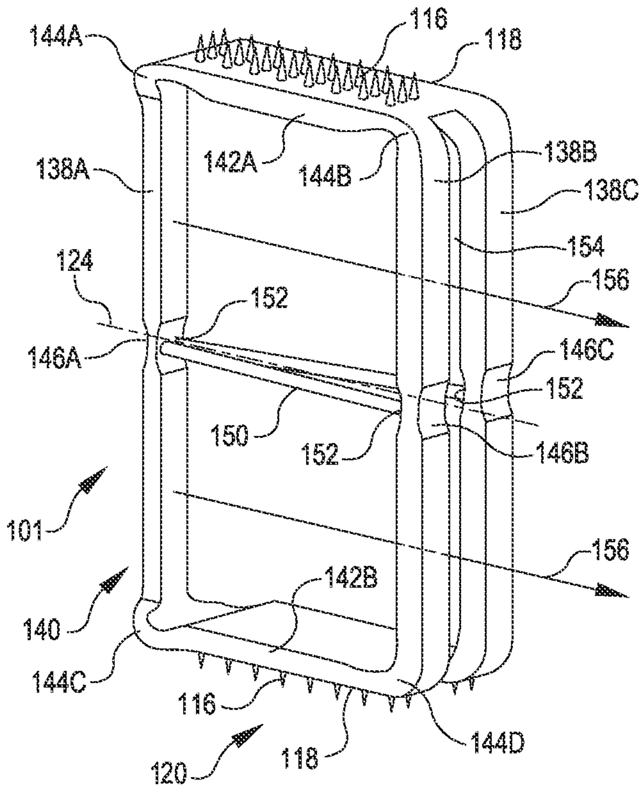
FIG. 7 shows a perspective view of an expanded, deployed state of an actuator with hinged lateral columns that may be utilized with the system of FIG. 1 according to certain examples of the present disclosure.
Figure 8:
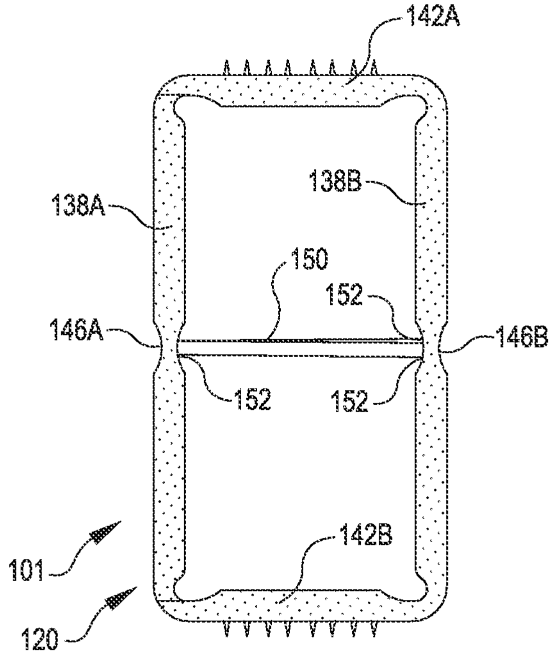
FIG. 8 shows an end view of the expanded, deployed state of the actuator of FIG. 7 according to certain examples of the present disclosure.
Figure 9:
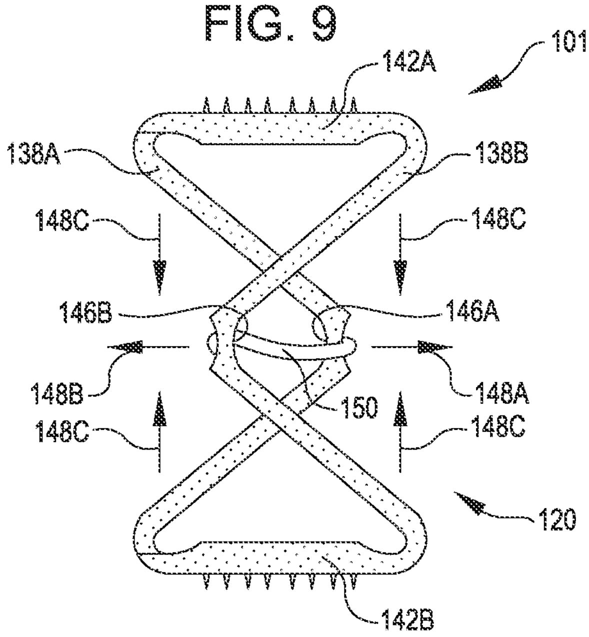
FIG. 9 shows an end view of an intermediate state of the actuator of FIGS. 7-8 between collapsed and deployed states according to certain examples of the present disclosure.
Figure 10:
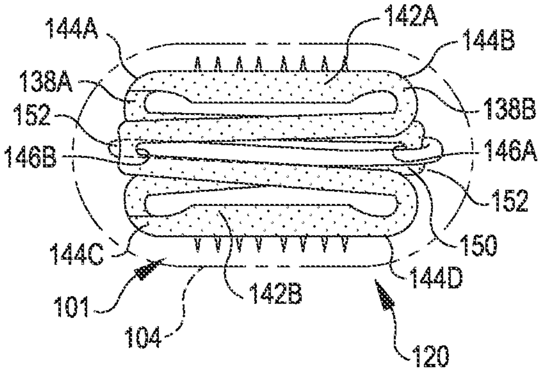
FIG. 10 shows an end view of the collapsed, ready state of the actuator of FIGS. 7-9 according to certain examples of the present disclosure.

FIG. 7 is a perspective view showing further examples of structure that may be incorporated into the system 100. In some examples (such as in FIG. 7), the mechanical actuator 120 may include hinged columns 138 (individually identified with suffixes A, B, and C). The ability of columns 138 to hinge may allow the mechanical actuator 120 to be compressible toward and expandable away from the central longitudinal axis 124 of the mechanical actuator 120 (e.g., in a radial or normal direction, which may correspond to a direction perpendicular to the long axis of the lumen 102). For example, where FIGS. 7 and 8 respectively show perspective and end views of the hinged columns 138 in an expanded, deployed state, FIG. 10 shows a perspective end view of a corresponding ready, collapsed state, whereas FIG. 9 shows an end view of an intermediate state in between the collapsed and expanded states.

As may be best appreciated with respect to FIG. 7, the columns 138 may form part of a body 140 of the mechanical actuator 120. The body 140 can include the columns 138 and crossbeams 142 (e.g., an upper crossbeam 142A and a lower crossbeam 142B).

Microneedles 116 are depicted as supported by carriers 118 that are integrally formed with the crossbeams 142 of the body 140, although other arrangements are possible, including, but not limited to arrangements in which the microneedles 116 and/or carriers 118 are instead separately mounted, or arrangements in which the carrier 118 corresponds to a band or other distinct structure such as described with respect to FIGS. 1 and 2.

The body 140 may be substantially rectangular, for example. The body 140 can define corners 144, such as an upper left corner 144A, an upper right corner 144B, a lower left corner 144C, and a lower right corner 144D as shown in FIG. 7. The columns 138 may be positioned laterally with respect to the body 140 and thus may alternatively be termed lateral columns. The upper crossbeam 142A and the lower crossbeam 142B can be joined by the columns 138, such as at the corners 144 of the body 140.

Each column 138 can have a respective hinge 146 (individually identified with suffixes A, B, and C). The hinge 146 may be positioned toward a middle of the column 138 and thus may alternatively be termed a middle hinge. In some examples, the hinge 146 may correspond to a portion of the column 138 having a reduced cross-section in comparison to other portions of the column 138, although the hinge 146 may correspond to any suitable structure for facilitating bending or flexing of the column 138 about the hinge 146.

The columns 138 and/or other portion of the body 140 may be formed of suitable material. In some examples, the material is a flexibly resilient material (such as having sufficient flexibility to allow compression from the expanded state toward the compressed state, and further having sufficient resiliency to bias the material toward expanding away from the compressed state and toward the expanded state, e.g., to drive microneedles 116 outward for tissue engagement). In some examples, material is biodegradable material (e.g., capable of degrading within a gastrointestinal tract) and/or suitable for construction by 3D-printing or other specific fabrication techniques. Some examples of suitable materials can include SLA, 3D-printed durable resin, gelatin paper or sheets, rice paper or sheets, polylactic acid, nylon, polyester, PVA (polyvinyl alcohol), or corn-based polymers.

The hinges 146 may facilitate reconfiguration between the collapsed state (e.g., FIG. 10) and the expanded state (e.g., FIG. 7). In the expanded state (such as shown in FIG. 7 and FIG. 8), the hinge 146 of each column 138 may be aligned with (e.g., positioned underneath or over) respective ends of the crossbeams 142 that are directly connected to the column 138. For example, the hinge 146A of the leftward column 138A in the expanded state may be positioned in alignment under the upper left corner 144A and over the lower left corner 144C. During movement from the expanded state to the collapsed state, the hinges 146 may move out of such alignment, such as by moving toward one another as the hinges 146 flex. In some examples, a respective hinge 146 when shifting between the collapsed state and the expanded state moves from underneath or over one end of the upper crossbeam 142 to underneath or over an opposite end. For example, in contrast to the above-described position of the hinge 146A of the leftward column 138A in the expanded position (e.g., FIG. 7), the leftward column 138A in the collapsed position (e.g., FIG. 10) may be aligned with (e.g., positioned underneath or over) respective ends of the crossbeams 142 that are not directly connected to the column 138 (such as under the upper right corner 144B and over the lower right corner 144D).

In operation, the hinges 146 of different columns 138 may pass by one another when shifting between the collapsed state and the expanded state. For example, as may be most readily seen in FIG. 9, the hinge 146A of the leftward column 138A may move toward the right (e.g., as illustrated by arrow 148A) and pass the hinge 146B of the rightward column 130B as the hinge 146B of the rightward column 138B instead moves toward the left (e.g., as illustrated by arrow 148B). Movement of the columns 138 may cause, be caused by, or otherwise be accompanied by movement of the top crossbeam 142A and bottom crossbeam 142B toward one another, such as illustrated by the arrows 148C).

Various segments of the body 140 may be approximately equal length to facilitate collapsing of the body 140 into a stacking and/or nesting arrangement. For example, each of the crossbeams 142 and portions of the columns 138 on either side of the hinge 146 may be approximately equal in length. As may be best recognized with reference to FIG. 10, utilizing approximately equal lengths may facilitate a compact arrangement in which the respective segments fit within a predetermined length suitable for fitting within a capsule 104.

A tension member 150 may be attached between multiple of the columns 138. The tension member 150 may be formed of any suitable material for applying a biasing force. Suitable examples may include silicone tubing, although any other type of material and/or form with suitable characteristics may be utilized. In some examples, the tension member 150 is coupled with one or more of the hinges 146. In use, the tension member 150 may provide a force for biasing the mechanical actuator 120 toward opening toward the expanded state. In the collapsed state of the device 101, the tension member 150 may be stretched more than in the expanded state. For example, a stretched length of the tension member 150 between anchor points 152 in the collapsed state of the device 101 (e.g., FIG. 10) may be greater than a length of the tension member 150 between the same anchor points once moved to the expanded state of the device 101 (e.g., FIG. 8). In some examples, the anchor points 152 may correspond to surfaces that face one another in the expanded configuration and face away from one another in the collapsed configuration. Although the anchor points 152 in FIG. 8 are shown located at the hinges 146, any other suitable location along the columns 138 may be utilized. During shifting from the expanded state to the collapsed state, the tension member 150 may at least partially wrap around one or more of the columns 138 and increase an amount of pre-loaded force available from the tension member 150 for biasing toward the expanded state. In the expanded state, the tension member 150 may continue to apply some force to the columns 138. Thus, although the columns 138 are depicted fully upright in the expanded state (e.g., FIG. 8), in some examples, the columns 138 in the expanded state may exhibit some degree of bending or bowing inwardly as a result of the tension member 150.

Any suitable number of columns 138 can be utilized. In some examples, different numbers of columns 138 may be placed on opposite lateral sides. For example, in FIG. 7, one column 138A is shown on the left, while the right side is depicted with a pair of columns 138B and 138C. A slot 154 may be defined between adjacent columns, such as between the pair of columns 138B and 138C. As illustrated by arrows 156, the slot 154 may be sized to permit travel therethrough of the column 138 from the opposite side during shifting between the collapsed and the expanded state. The slot 154 may additionally be sized to allow the tension member 150 to pass through at least partially. In some examples, including more than a single column 138 on at least one of lateral side can provide greater dimensional stability and/or result in less risk of unintended twisting than if only a single column 138 is used on each side.

In use, the body 140 may provide a central and substantial through-passage in the expanded state (e.g., with minimal blockage from the passage being subdivided by the tension member 150) and thus prevent or avoid full obstruction or occlusion of the lumen of the duodenum or other relevant body lumen 102. Additionally, the body 140 may provide substantially straight outward movement of the microneedles 116 so as to engage perpendicular to the lining of the lumen wall 103 of the body lumen 102 and reduce or avoid shearing forces that might occur if the mechanical actuator 120 instead imparted some tangentially-oriented components in addition to straight outward components (such as those oriented along a radial or normal direction, which may correspond to a direction perpendicular to the long axis of the lumen 102).

Figure 11:
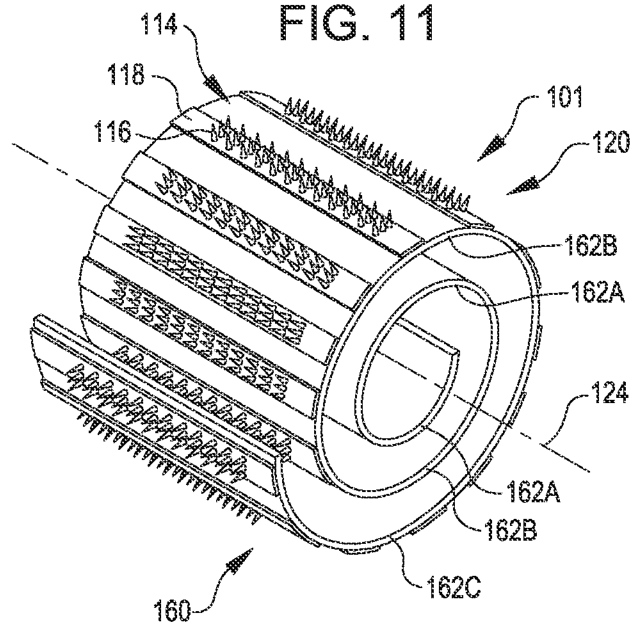
FIG. 11 shows a perspective view of a collapsed, ready state of a coiled actuator that may be utilized with the system of FIG. 1 according to certain examples of the present disclosure.
Figure 12:
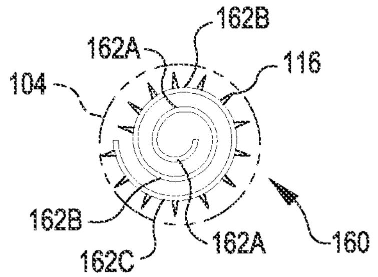
FIG. 12 shows an end view of the collapsed, ready state of the coiled actuator of FIG. 11 according to certain examples of the present disclosure.

FIG. 11 is a perspective view showing further examples of structure that may be incorporated into the system 100. In some examples (such as in FIG. 11), the mechanical actuator 120 may include a coil 160. The coil 160 may be compressible toward and expandable away from the central longitudinal axis 124 of the mechanical actuator 120 (e.g., in a radial or normal direction, which may correspond to a direction perpendicular to the long axis of the lumen 102). For example, where FIGS. 11 and 12 respectively show perspective and end views of the coil 160 in a ready, collapsed state, FIG. 13 shows an end view of the coil 160 in a corresponding expanded, deployed state.

As may be best appreciated with respect to FIG. 7, the coil 160 may include a number of overlapping turns 162. For example, in FIG. 7, a total of three turns 162A, 162B, and 162C are visible on a lower half of the coil 160 whereas a total of two turns 162A, 162B are visible on an upper half of the coil 160. The coil 160 is not limited to the number of turns 162 depicted but may include any suitable number of turns 162 to provide a suitable predisposition to uncoil and expand outwardly for driving microneedles 116 into the lining of the lumen wall 103 of the body lumen 102.

The coil 160 may be formed of suitable material. In some examples, the material is a flexibly resilient material (such as having sufficient flexibility to allow compression from the expanded state toward the compressed state, and further having sufficient resiliency to bias the material toward expanding away from the compressed state and toward the expanded state, e.g., to drive microneedles 116 outward for tissue engagement). In some examples, material is biodegradable material (e.g., capable of degrading within a gastrointestinal tract) and/or suitable for construction by 3D-printing or other specific fabrication techniques. Some examples of suitable materials can include SLA, 3D-printed durable resin, gelatin paper or sheets, rice paper or sheets, polylactic acid, nylon, polyester, PVA (polyvinyl alcohol), or corn-based polymers.

Figure 13:
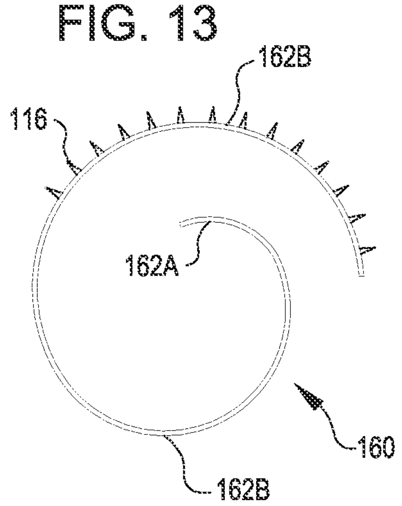
FIG. 13 shows an end view of an expanded, deployed state of the coiled actuator of FIGS. 11-12 according to certain examples of the present disclosure.

The coil 160 may facilitate reconfiguration between the collapsed state (e.g., FIG. 12) and the expanded state (e.g., FIG. 13). For example, the turns 162 of the coil 160 may be more tightly wound (and/or more numerous) in the collapsed state (e.g., FIG. 12) than in the expanded state (e.g., FIG. 13). The tightness of the winding may pre-dispose the coil 160 toward unwinding upon release from constraint to drive microneedles 116 outwardly.

Microneedles 116 are depicted as supported by carriers 118 that are separately mounted to the coil 160, although other arrangements are possible, including, but not limited to arrangements in which the microneedles 116 and/or carriers 118 are instead integrally formed, or arrangements in which the carrier 118 corresponds to a band or other distinct structure such as described with respect to FIGS. 1 and 2. Furthermore, although the microneedles 116 are depicted as solely arranged on outer-facing surfaces of or the outer-most turn 162 of the coil 160, in some examples, microneedles 116 may additionally or alternatively be disposed on interior surfaces and/or internal turns 162 of the coil 160.

In use, the coil 160 may provide a central and substantial through-passage in the expanded state and thus prevent or avoid full obstruction or occlusion of the lumen of the duodenum or other relevant body lumen 102. Additionally, although the coil 160 may provide movement of the microneedles 116 that includes some tangentially-oriented components in addition to straight outward components aligned along a radial or normal direction (and thus may impart some shearing forces), an amount of shearing may be mitigated by adjusting thickness of the coil 160 (e.g., to impart a greater rigidity that may result in a stronger force for engaging tissue of the lumen wall 103 of the body lumen 102). Moreover, the coil 160 may present a smoother overall surface and/or fewer sharp edges than some other alternatives herein, which may further reduce the shearing forces. In addition, the coil 160 may present a continuous surface that provides a greater number of options for attachment of arrays 114 in comparison to other alternatives herein. Furthermore, the form factor of the coil 160 may facilitate use of roll-to-roll manufacturing processes that may be faster, more economic, and/or otherwise beneficial in comparison to fabrication processes for other alternatives herein.

Figure 14A:
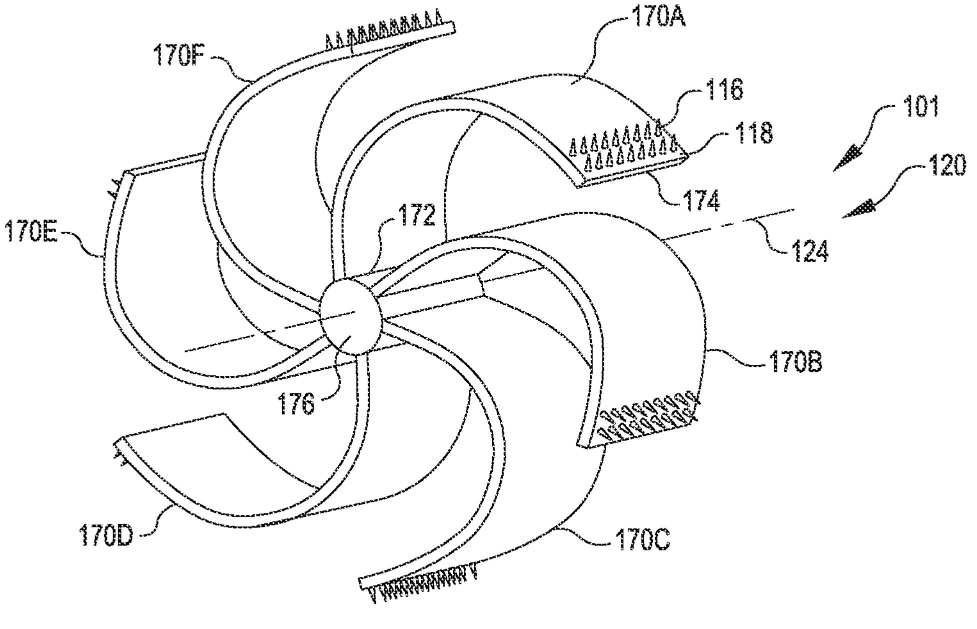
FIG. 14A shows a perspective view of an expanded, deployed state of an actuator with curved arms that may be utilized with the system of FIG. 1 according to certain examples of the present disclosure.
Figure 14B:
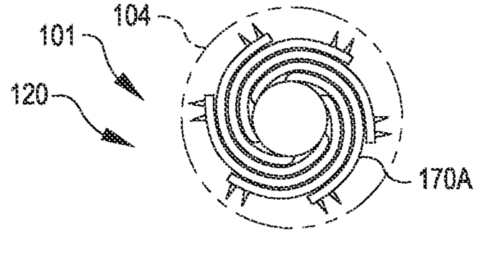
FIG. 14B shows an end view of a collapsed, ready state of the actuator of FIG. 14A according to certain examples of the present disclosure.

FIG. 14A is a perspective view showing further examples of structure that may be incorporated into the system 100. In some examples (such as in FIG. 14A), the mechanical actuator 120 may include curved arms 170 (individually identified with suffixes A, B, C, D, E, and F). The curved arms 170 may be compressible toward and expandable away from the central longitudinal axis 124 of the mechanical actuator 120 (e.g., in a radial or normal direction, which may correspond to a direction perpendicular to the long axis of the lumen 102). For example, the curved arms 170 are depicted in FIG. 14A in an expanded, deployed state and may be curled over one another to reach a ready, collapsed state (such as depicted in FIG. 14B).

Microneedles 116 are depicted as supported by carriers 118 that are integrally formed with the curved arms 170, although other arrangements are possible, including, but not limited to arrangements in which the microneedles 116 and/or carriers 118 are instead separately mounted, or arrangements in which the carrier 118 corresponds to a band or other distinct structure such as described with respect to FIGS. 1 and 2.

As may be best appreciated with respect to FIG. 14A, each curved arm 170 may include a proximal end 172 and a distal end 174 opposite the proximal end 172. Each curved arm 170 can be attached at the proximal end 172 to a central core 176. For example, the proximal end 172 may be seated in a slit within the core 176. Additionally or alternatively, the proximal end 172 may be secured to the core 176 by a suitable adhesive or otherwise joined in a pivotable fashion.

The curved arms 170 may define an arc between the proximal end 172 and the distal end 174. The arc may change as the device shifts between the collapsed state and the expanded state (e.g., between the states shown in FIGS. 14A and 14B). In operation, the curved arms 170 may be movable so that the distal ends 174 rotate away from the core 176 in a spiraling direction to move from the collapsed state to the expanded state.

Any suitable number of curved arms 170 can be utilized. Thus, although six curved arms 170 are depicted, more or fewer could be alternatively utilized.

The curved arms 170 and/or the core 176 may be formed of suitable material and may or may not differ from one another in material utilized. In some examples, the material is a flexibly resilient material (such as having sufficient flexibility to allow compression from the expanded state toward the compressed state, and further having sufficient resiliency to bias the material toward expanding away from the compressed state and toward the expanded state, e.g., to drive microneedles 116 outward for tissue engagement). In some examples, material is biodegradable material (e.g., capable of degrading within a gastrointestinal tract) and/or suitable for construction by 3D-printing or other specific fabrication techniques. Some examples of suitable materials can include SLA, 3D-printed durable resin, gelatin paper or sheets, rice paper or sheets, polylactic acid, nylon, polyester, PVA (polyvinyl alcohol), or corn-based polymers. In some examples, the material can be provided as or include at least one film layer. In some examples, the material for the curved arms 170 may be subjected to a spin coating and drying process or other suitable process that can impart a pre-stressed or pre-loaded bent structure that can pre-dispose the curved arms 170 toward an equilibrium state that is open further than in the absence of such treatment so that the curved arms 170 can impart a greater driving force.

In use, the curved arms 170 may provide a set of substantial through-passages in the expanded state (e.g., with minimal blockage from the passages being separated by the curved arms 170) and thus prevent or avoid full obstruction or occlusion of the lumen of the duodenum or other relevant body lumen 102. Additionally, although the curved arms 170 may provide movement of the microneedles 116 that includes some tangentially-oriented components in addition to straight outward components aligned along a radial or normal direction (and thus may impart some shearing forces), a magnitude of the normal component of the curved arms 170 may be greater than provided by the coil 160 or other components described herein (e.g., which may result in a stronger force for engaging tissue of the lining of the lumen wall 103 of the body lumen 102).

Figure 15:
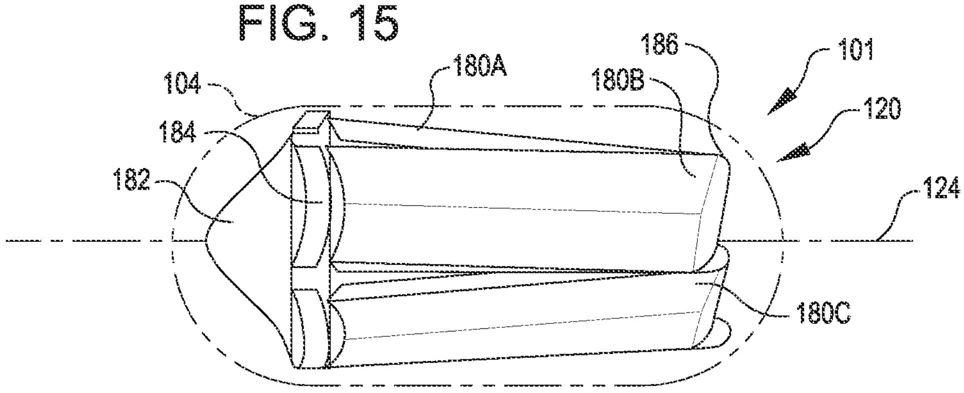
FIG. 15 shows a side view of a collapsed, ready state of an actuator with double-hinged arms that may be utilized with the system of FIG. 1 according to certain examples of the present disclosure.

FIG. 15 is a perspective view showing further examples of structure that may be incorporated into the system 100. In some examples (such as in FIG. 15), the mechanical actuator 120 may include double-hinged arms 180 (individually identified with suffixes A, B, and C). The double-hinged arms 180 may be compressible toward and expandable away from the central longitudinal axis 124 of the mechanical actuator 120 (e.g., in a radial or normal direction, which may correspond to a direction perpendicular to the long axis of the lumen 102). For example, whereas FIG. 15 shows a side view of the double-hinged arms 180 in a ready, collapsed state, FIG. 16 shows a side view of a corresponding expanded, deployed state.

Microneedles 116 are depicted as supported by carriers 118 that are integrally formed with the double-hinged arms 180, although other arrangements are possible, including, but not limited to arrangements in which the microneedles 116 and/or carriers 118 are instead separately mounted, or arrangements in which the carrier 118 corresponds to a band or other distinct structure such as described with respect to FIGS. 1 and 2.

Figure 16:
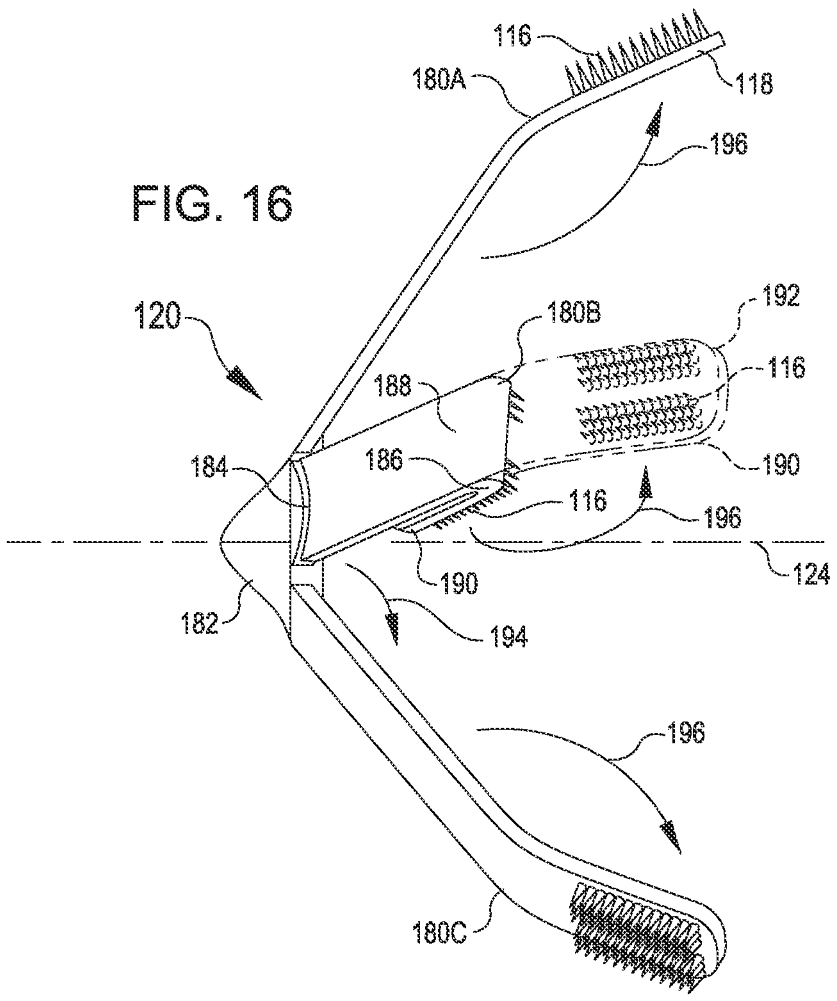
FIG. 16 shows a side view of an expanded, deployed state of the actuator of FIG. 15 according to certain examples of the present disclosure.

As may be best appreciated with respect to FIG. 16, the double-hinged arms 180 may deploy relative to a hub 182. Any suitable number of double-hinged arms 180 can be utilized. Thus, although three double-hinged arms 180 are depicted, more or fewer could be alternatively utilized.

Figure 17:
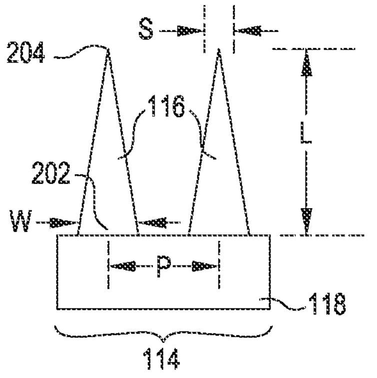
FIG. 17 is a side perspective view illustrating an example of a portion of an array of microneedles that may be utilized in the system of FIG. 1 according to certain examples of the present disclosure.

The arms 180 may each have like features, but for simplicity, various of such features are identified solely with respect to the arm 180B in FIGS. 16-17. Each double-hinged arm 180 may include a first hinge 184 and a second hinge 186, which may define respective sub-portions of the double-hinged arm 180. For example, the double-hinged arm can include a proximal portion 188 and a distal portion 190.

The first hinge 184 may couple the proximal portion 188 of the double-hinged arm 180 to the hub 182. The proximal portion 188 can extend (e.g., span) between the first hinge 184 and the second hinge 186.

The second hinge 186 may couple the proximal portion 188 to the distal portion 190 of the double-hinged arm 180. The distal portion 190 may extend from the second hinge 186 to a free end 192 of the double-hinged arm 180.

The first hinge 184 and/or the second hinge 186 may correspond to a portion of the double-hinged arm 180 having a reduced cross-section in comparison to other portions of the double-hinged arm 180 and/or may correspond to any suitable structure for facilitating bending or flexing of the double-hinged arm 180 about the first hinge 184 and/or the second hinge 186.

The double-hinged arm 180 and/or other associated components may be formed of suitable material. In some examples, the material is a flexibly resilient material (such as having sufficient flexibility to allow compression from the expanded state toward the compressed state, and further having sufficient resiliency to bias the material toward expanding away from the compressed state and toward the expanded state, e.g., to drive microneedles 116 outward for tissue engagement). In some examples, material is biodegradable material (e.g., capable of degrading within a gastrointestinal tract) and/or suitable for construction by 3D-printing or other specific fabrication techniques. Some examples of suitable materials can include SLA, 3D-printed durable resin, gelatin paper or sheets, rice paper or sheets, polylactic acid, nylon, polyester, PVA (polyvinyl alcohol), or corn-based polymers.

The double-hinged arms 180 may facilitate reconfiguration between the collapsed state (e.g., FIG. 15) and the expanded state (e.g., FIG. 16). In the collapsed state (e.g., FIG. 15), the proximal portion 188 of the double-hinged arm 180 may be located outwardly of the distal portion 190 of the double-hinged arm 180 relative to the central longitudinal axis 124 of the mechanical actuator 120 (e.g., such that the distal portions 190 are hidden from view in FIG. 15). In moving from the collapsed state (e.g., FIG. 15) to the expanded state (e.g., FIG. 16), the proximal portion 188 of the double-hinged arm 180 may open away from the hub 182 (e.g., as illustrated by arrow 194). For example, the proximal portion 188 may pivot about the first hinge 184, e.g., due to properties of included material. Further, the distal portion 190 of the double-hinged arm 180 may open away from the proximal portion 188 of the double-hinged arm 180 (e.g., as illustrated by arrows 196). For example, the distal portion 190 may pivot about the second hinge 186, e.g., due to properties of included material. In some examples, the microneedles 116 may be positioned to face toward an interior of the device 101 prior to deployment (e.g., as depicted in solid lines relative to the middle double-hinged arm 180 in FIG. 16), and face outward from the device 101 after deployment (e.g., as depicted in phantom lines relative to the middle double-hinged arm 180 in FIG. 16). For example, the microneedles 116 may shift from facing an interior to facing outward from the device as a result of deploying about the second hinge 186.

In use, the double-hinged arms 180 may provide a set of substantial through-passages in the expanded state (e.g., with minimal blockage from the passages being separated by the double-hinged arms 180) and thus prevent or avoid full obstruction or occlusion of the lumen of the duodenum or other relevant body lumen 102. Additionally, although the double-hinged arms 180 may provide movement of the microneedles 116 that includes some tangentially-oriented components in addition to straight outward components aligned along a radial or normal direction (and thus may impart some shearing forces), a magnitude of the normal component of the double-hinged arms 180 may be greater than provided by the coil 160 or other components described herein (e.g., which may result in a stronger force for engaging tissue of the lining of the lumen wall 103 of the body lumen 102).

FIG. 17 is a side perspective view illustrating an example of a portion of an array 114 of microneedles 116 that may be utilized in the system 100. The microneedles may include a base 202 and a tip 204. The tip 204 may correspond to a portion of the microneedle 116 farthest from the base 202.

Various geometry and/or other physical features may be appreciated in FIG. 17. For example, the microneedles 116 may be characterized by a length L defined between the base 202 and tip 204. The microneedles 116 may be further characterized by base width W defined by a width dimension at the base 202. The microneedles 116 may have an aspect ratio corresponding to a value derived from dividing the length L by the base width W. A sharpness S may correspond to a smallest cross-sectional size of the microneedle 116 at the tip. A pitch P may be defined as a distance between corresponding bases 202 of the microneedles. For example, the pitch P may correspond to a center-to-center distance, a distance between adjacent edges, or any other relevant distance between respective features of adjacent microneedles 116.

Suitable dimensions of the physical features of the microneedles 116 may be implemented to achieve the desired result of engagement of the microneedle with the target tissue and release of the payload into the tissue. In some examples, a combination of features may mitigate against a "bed of nails" effect in which force is sufficiently distributed among a plurality of supports to prevent or reduce penetration efficacy by the supports into a surface. As an example, for microneedles 116 having a length L of approximately 1.5 mm, an aspect ratio of greater than or equal to 2 and less than or equal to 3 and/or a pitch of greater than or equal to 1.5 mm and less than or equal to 2 mm may mitigate against a 'bed of nails effect" when engaging tissue of a duodenum or other relevant lining of the lumen wall 103 of the body lumen 102.

Additionally or alternatively, a sharpness S of 1 micron or less may facilitate an ability of the microneedles 116 to sufficiently puncture the target tissue in use. In some examples, a sharpness S of 1 micron or less may be achieved by a process of three-dimensional ("3D") printing with two-photon polymerization, e.g., to produce the microneedles 116 or to produce a suitable mold from which to produce the microneedles 116. Achieving a sharpness S of 1 micron may be a substantial improvement over a limit of approximately 5 microns that may be available by other processes, such as pressing powder and hydraulically compressing into solid needles or electrical discharge machining (EDM).

Figure 18:
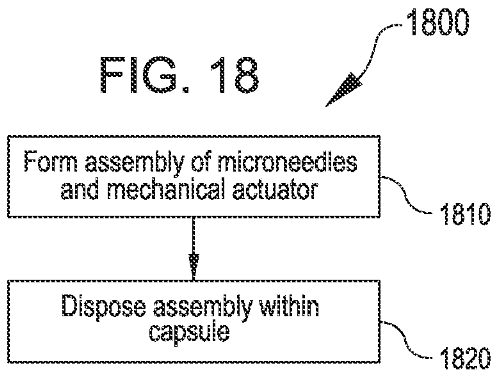
FIG. 18 is a flow chart showing an example process of fabrication according to certain examples of the present disclosure.

FIG. 18 is a flow chart showing an example process 1800 of fabrication according to some examples.

The process 1800 at act 1810 can include forming an assembly. For example, the assembly can include an array 114 of microneedles 116 and a mechanical actuator 120. The mechanical actuator 120 can be expandable in an outward direction from a central longitudinal axis 124. For example, the mechanical actuator 120 can include any structure described herein.

The act 1810 can also include forming the microneedles 116. For example, the microneedles may be formed with characteristics and/or by processes described with respect to FIG. 17 and/or with any other combination of characteristics and fabrication process. Any suitable fabrication process or technique may be utilized to form the microneedles 116. As non-limiting examples, processes may include use of 3D printing and/or a set of one or more molds by which shapes of the microneedles 116 can be imparted to suitable material. As a further example, roll-to-roll imprinting may be utilized.

The act 1810 can include coupling the microneedles 116 with the mechanical actuator 120. In some examples, the array 114 of microneedles 116 is formed prior to coupling with the mechanical actuator 120. For example, the array 114 may be bonded by silicon glue, cyanoacrylate, or other adhesive (or otherwise joined or mechanically coupled to the mechanical actuator 120). In some examples, the array 114 of microneedles 116 is mechanically coupled by integrally forming the array 114 of microneedles 116 into material of the mechanical actuator 120. For example, the array 114 may be printed or otherwise fabricated in the same printing or other fabrication process of forming material of the mechanical actuator 120. In some examples, the array 114 is coupled by use of an intervening structure. For example, the mechanical actuator 120 may be disposed within an expandable band or other carrier 118 that bears the microneedles 116 (such as in FIG. 1), which may include alternatives of the mechanical actuator 120 being fixed or not fixed to the expandable band or other carrier 118.

The act 1810 can also include forming the mechanical actuator 120. Fabrication may produce a part or the entirety of the mechanical actuator 120 in an equilibrium state from which the mechanical actuator 120 may be compressed to reach the collapsed state in which the mechanical actuator 120 is ready to expand upon release from constraint (such as may be provided by the capsule 104). The carriers 118 and/or arrays may be coupled with the mechanical actuator 120 before and/or after compressing from the equilibrium or expanded state.

Any suitable fabrication process or technique may be utilized to form the mechanical actuator 120. In some examples, all or at least a part of the mechanical actuator may be produced by 3D printing, SLA, or other additive or subtractive manufacturing process. In some examples, material for the mechanical actuator 120 can be provided as or include at least one film layer and/or be subjected to a spin coating and drying process or other suitable process that can impart a pre-stressed or pre-loaded structure conducive to the functioning of the mechanical actuator 120. In some examples, a roll-to-roll process can be utilized. As an illustrative example, in some examples, to produce the coil 160, material may be provided as a sheet or film from a roll to roll process, wound around a mandrel, outfitted with microneedles on an outermost layer, and sliced into segments that can be removed from the mandrel for insertion into capsules.

Any suitable material or combination of materials may be utilized for producing and/or connecting respective elements while fabricating the assembly having the mechanical actuator 120 and the microneedles 116. In some examples, the material is a flexibly resilient material (such as having sufficient flexibility to allow compression from the expanded state toward the compressed state, and further having sufficient resiliency to bias the material toward expanding away from the compressed state and toward the expanded state, e.g., to drive microneedles 116 outward for tissue engagement). In some examples, material is biodegradable material (e.g., capable of degrading within a gastrointestinal tract) and/or suitable for construction by 3D-printing or other specific fabrication techniques. Some examples of suitable materials can include stereolithography (SLA) 3D-printed durable resin, gelatin paper or sheets, rice paper or sheets, polylactic acid, nylon, polyester, PVA (polyvinyl alcohol), or corn-based polymers. In some examples, the material can be provided as or include at least one film layer. In some examples, the material can include a cast foam, such as may be produced in a pre-tensioned state that can impart a particular bias for contributing to movement from the collapsed state to the expanded state.

The process 1800 at act 1820 can include disposing the assembly within a capsule 104. For example, the capsule 104 can have a first state in which the capsule 104 constrains the mechanical actuator 120 from expanding, and the capsule 104 can be reconfigurable in a target location within a subject to a second state in which constraint by the capsule 104 is eliminated to permit the mechanical actuator 120 to expand for driving the array 114 of microneedles 116 into engagement with tissue at the target location. The target location may correspond to a duodenum or other body lumen 102, for example.

The acts 1810 and 1820 may be performed serially or may overlap at least partially. For example, in some examples, forming the assembly at act 1810 can include inserting respective components into the capsule 104 so that the assembly is formed within the capsule 104.

Figure 19:
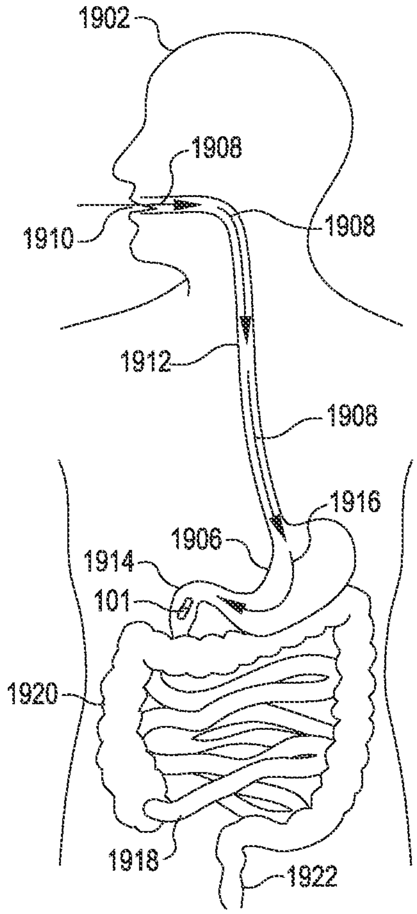
FIG. 19 illustrates an example of a progression of a device in use relative to a subject according to certain examples of the present disclosure.

FIG. 19 illustrates an example of a progression of a device 101 in use relative to a subject 1902. For example, the device 101 fabricated in accordance with the process 1800 and/or otherwise in accordance with other disclosure herein may be used to treat the subject 1902. The device 101 can be introduced into the subject's stomach 1906. For example, the device 101 can be contained in a pill or otherwise in an ingestible form that permits the device 101 to be swallowed to pass (e.g., as depicted by arrows 1908) through the subject's mouth 1910 and esophagus 1912 into the subject's stomach 1906. The device 101 can pass from the stomach 1906 into the duodenum 1914 (e.g., as depicted by arrow 1916). For example, the device 101 is depicted in the duodenum 1914 as an example of a suitable target location for actuation of the device 101, although the target location could alternatively include any other location in the gastro-intestinal tract, such as the distal small intestine (i.e., jejunum and ileum) 1918, large intestine 1920, or colon 1922. The device 101 may actuate at the target location in response to stimuli and/or conditions present in or en route to the target location. Actuation may cause the microneedles 116 (obscured from view within the device 101 in FIG. 19) to expand outwardly into tissue at the target location to deliver a drug or other payload. Suitable payloads may include small molecules and biotherapeutics (e.g., including peptides, monoclonal antibodies, and nucleic acids), for example. In various examples, following or in conjunction with the payload delivery, respective components of the device 101 may be absorbed into the subject 1902 (e.g., based on use of biodegradable materials) and/or passed out of the subject 1902, e.g. through the colon 1922 of the subject 1902 within other excrement.

Figure 20:
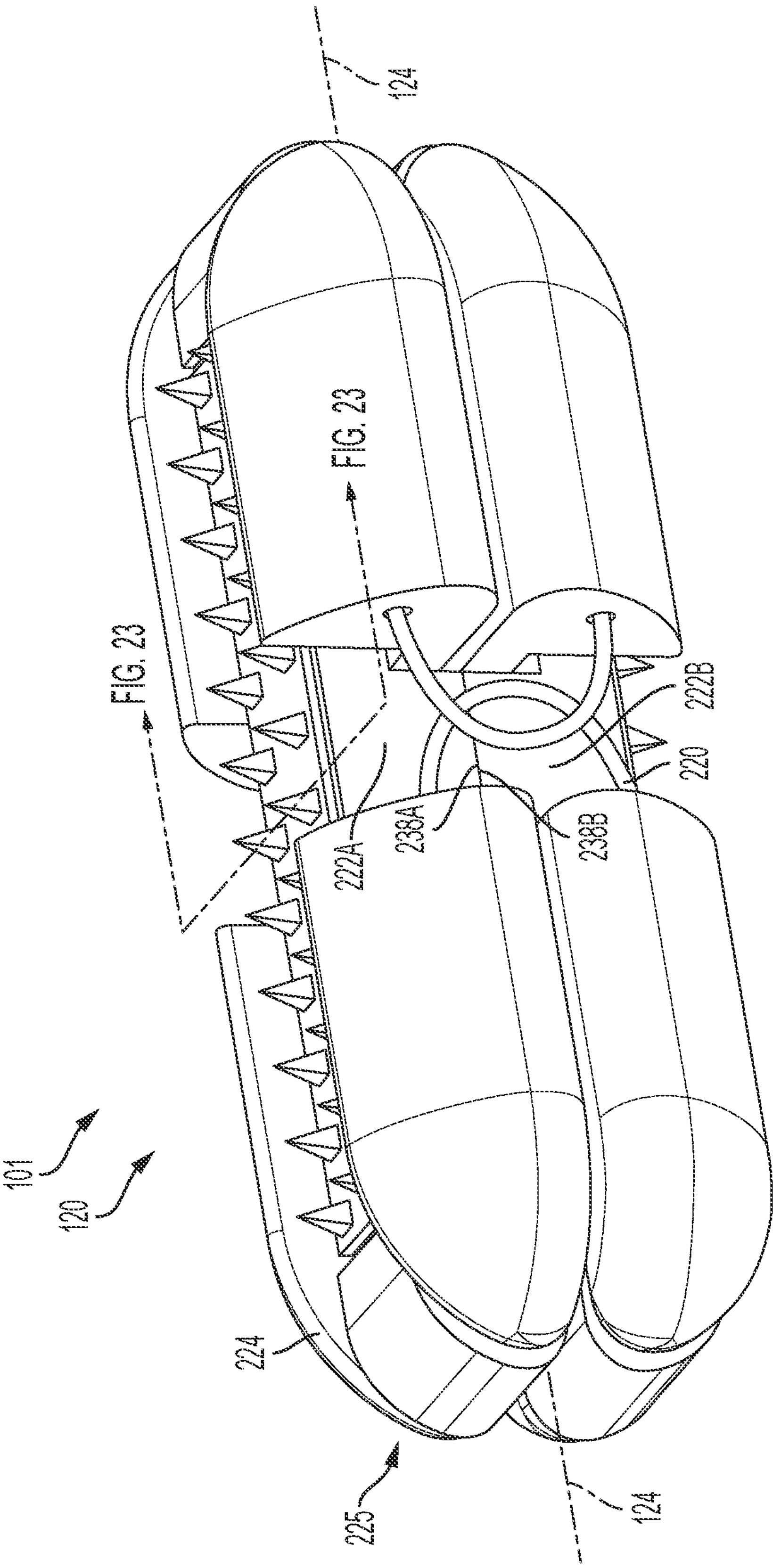
FIG. 20 shows a perspective view of a collapsed, ready state of an actuator with foldable biasing members that may be utilized with the system of FIG. 1 according to certain examples of the present disclosure.
Figure 21:
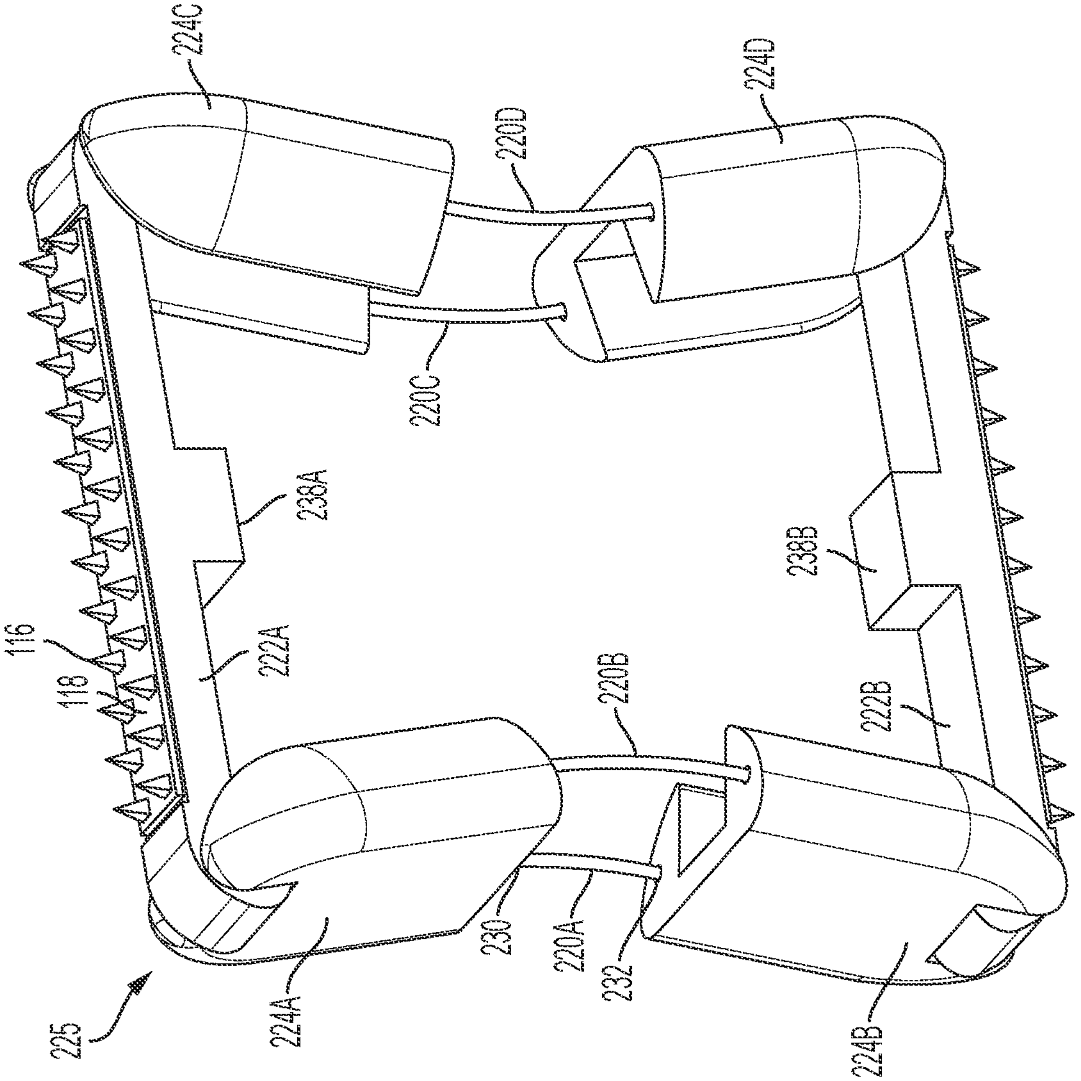
FIG. 21 shows a perspective view of an expanded, deployed state of the actuator of FIG. 20 according to certain examples of the present disclosure.

FIG. 20 is a perspective view showing further examples of structure that may be incorporated into the system 100. In some examples (such as in FIG. 20), the mechanical actuator 120 may include a foldable biasing member 220. The ability of foldable biasing member 220 to fold may allow the mechanical actuator 120 to be compressible toward and expandable away from the central longitudinal axis 124 of the mechanical actuator 120 (e.g., in a radial or normal direction, which may correspond to a direction perpendicular to the long axis of the lumen 102). For example, where FIG. 20 shows a perspective view of the foldable biasing member 220 in a ready, collapsed state, FIG. 21 shows a perspective view of a corresponding expanded, deployed state. In addition, FIG. 22 shows an exploded assembly view, and FIG. 23 shows a partial sectional end view along the line shown in FIG. 20.

Figure 22:
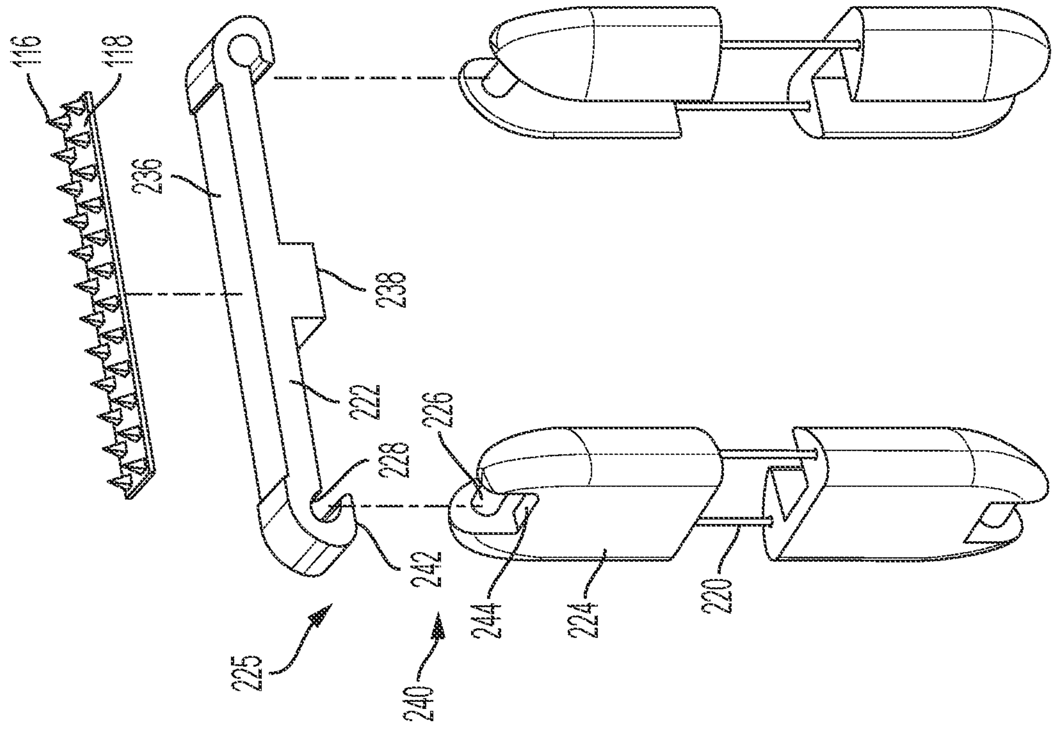
FIG. 22 shows an exploded assembly view of the actuator of FIG. 20-21 according to certain examples of the present disclosure.
Figure 23:
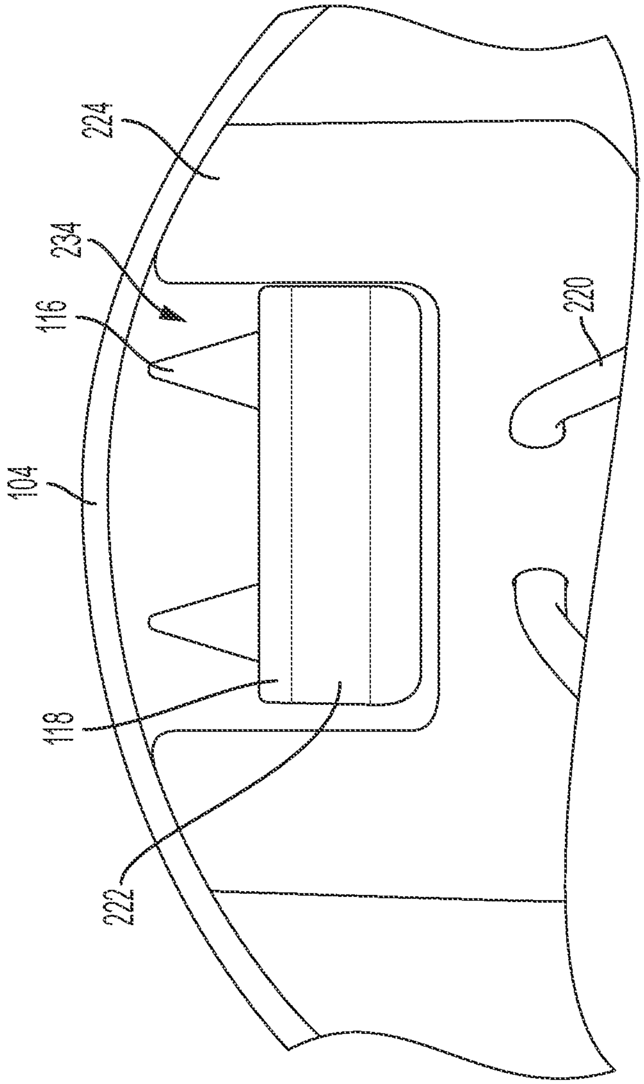
FIG. 23 shows a partial sectional end view of the actuator of FIG. 20-22 according to certain examples of the present disclosure.

As may be best seen in FIG. 22, the foldable biasing member 220 may be associated with a holder 222. For example, the foldable biasing member 220 may be hingedly attached with the holder 222.

Microneedles 116 are depicted as supported by carriers 118 that are separately mounted to the holder 222, although other arrangements are possible, including, but not limited to arrangements in which the microneedles 116 and/or carriers 118 are instead integrally formed, or arrangements in which the carrier 118 corresponds to a band or other distinct structure such as described with respect to FIGS. 1 and 2.

Referring still to FIG. 22, the foldable biasing member 220 and/or the holder 222 may be associated with a linkage 224. For example, the foldable biasing member 220 and the holder 222 may be hingedly attached via the linkage 224. The linkage 224 at one terminus or portion may receive or otherwise be coupleable or coupled with the foldable biasing member 220 and at another terminus or portion may be hinged or otherwise coupleable or coupled with the holder 222, for example.

Any suitable hinge 225 may be utilized. For example, as shown in FIG. 22, the hinge 225 includes a post 226 and a corresponding seat 228 arranged to receive the post 226 and permit rotation of or relative to the post 226. The depiction in FIG. 22 shows the seat 228 as a hook formed in the holder 222 and the post 226 borne by the linkage 224, although other variations may be suitable. For example, relative positioning may be reversed so that the post 226 is borne by the holder 222 while the seat 228 is borne by the linkage 224 (e.g., similar to the arrangement in FIG. 24). In some examples, the seat 228 rather than an open hook may correspond to a closed collar. Living hinges or other hinging interfaces may additionally or alternatively be used to couple the holder 222 relative to the linkage 224 and/or the foldable biasing member 220.

The foldable biasing member 220, the holder 222, the linkage 224, the hinge 225, and/or other associated components may be formed of suitable material. In some examples, at least some of the material is a flexibly resilient material (such as having sufficient flexibility to allow compression from the expanded state toward the compressed state, and further having sufficient resiliency to bias the material toward expanding away from the compressed state and toward the expanded state, e.g., to drive microneedles 116 outward for tissue engagement). In some examples, material is biodegradable material (e.g., capable of degrading within a gastrointestinal tract) and/or suitable for construction by 3D-printing or other specific fabrication techniques. Some examples of suitable materials can include SLA, 3D-printed durable resin, gelatin paper or sheets, rice paper or sheets, polylactic acid, nylon, polyester, PVA (polyvinyl alcohol), or corn-based polymers.

In some examples, the material used may include non-biodegradable material (e.g., which may be passed via excretion). In some examples, the material for the foldable biasing member 220 may include a metal such as nitinol or associated alloys. In some examples, superelastic nitinol may be used and may exhibit improved performance in comparison to heat-set nitinol (e.g., which may exhibit memory). For example, superelastic nitinol may be bent and strained significantly without permanent deformation. Nitinol may permit folding to the compressed state and provide adequate expansion force for driving microneedles 116. Nitinol may further suitably withstand being in a folded state for substantial amount of time, e.g., being able to remain in a stressed state without exhibiting substantial plastic deformation, creep, and/or other degradation that may negatively impact performance. Further, although the foldable biasing member 220 is depicted with a form factor of multiple wires, any other suitable form factor may be utilized, including, but not limited to, an individual wire or a bar. In some examples, a strip of sheet metal may be utilized additionally or alternatively. Stainless steel or other materials suitable for use in springs may be utilized additionally or alternatively.

Any suitable number of foldable biasing members 220, holders 222, and/or linkages 224 can be utilized, and the number of each may be alike or different relative to one another. For example, in FIG. 21, a total of four foldable biasing members 220, two holders 222, and four linkages 224 are depicted, although one, two, three, four, or any other number may be utilized. Each element of the same name may each have like features, but for simplicity and to avoid obscuring the figures, various of such features are identified primarily with respect to only the upper leftmost of such features in FIG. 21.

The foldable biasing member 220 may include a first end 230 and a second end 232. Flexibility of the foldable biasing member 220 can allow the first end 230 and the second end 232 to be foldable toward one another, such as for movement from the expanded state (e.g., FIG. 21) toward the collapsed state (e.g., FIG. 20). Conversely, resilience of the foldable biasing member 220 may urge the first end 230 and the second end 232 apart from one another, such as for movement from the collapsed state (e.g., FIG. 20) toward the expanded state (e.g., FIG. 21).

The foldable biasing member 220 (e.g., at a terminus) may be received or otherwise covered by the linkage 224. For example, as depicted in FIG. 21, the first end 230 is received in and covered by a first linkage 224A, while the second end 232 is received in and covered by a second linkage 224B. Covering extremities of the foldable biasing member 220 may prevent exposure to sharp tips or other puncture risks during passage through the body. For example, if the foldable biasing member 220 is formed of non-biodegradable material, the linkage 224 may also be formed of non-biodegradable material as a protective measure during passage through the gastrointestinal tract. In some embodiments, a coating of silicone or other material may be arranged about the foldable biasing member 220 (e.g., between the first linkage 224A and the second linkage 224B) and may prevent exposure to metal or other material of the foldable biasing member 220.

As may be best seen in FIG. 23, the linkage 224 may define a channel 234. The channel 234 may be sized to receive the holder 222, the microneedles 116, and/or the carrier 118. For example, the channel 234 can have a height, width, and/or depth in which such components can at least partially fit. The channel 234 may be sized so that the microneedles 116 are arranged out of contact with the capsule 104 when the device 101 is in the compressed state. Maintaining the microneedles 116 out of contact with the capsule 104 may prevent dulling of the microneedles 116 that could otherwise reduce efficacy at deployment.

The holder 222 can include features suitable for engaging other components. For example, as may best be seen in FIG. 22, the holder 222 can include a support surface 236 that may support the carrier 118 and/or microneedles 116 in use. Although the support surface 236 is shown arranged to receive a separately mounted carrier 118 (e.g., by adhesive, over-molding, or other attachment technique), the support surface 236 may support the carrier 118 by other methods, such as by being integrally formed together or by engaging a band or other distinct structure such as described with respect to FIGS. 1 and 2.

The holder 222 may attach at opposite ends or sides to multiple other components. For example, in FIG. 22, the first or upper holder 222A is hinged at left and right sides (e.g., which may correspond to front and rear) respectively to the first or upper left linkage 224A and the third or upper right linkage 224C, while the second or lower holder 222B is hinged at left and right sides respectively to the second or lower left linkage 224B and the fourth or lower right linkage 224D. In addition, in FIG. 22, the first foldable biasing member 220A and the second foldable biasing member 220B are shown coupled with both the first or upper holder 222A and the second or lower holder 222B (e.g., based on connection with the first or upper left linkage 224A and the second or lower left linkage 224B), while the third foldable biasing member 220C and the fourth foldable biasing member 220D are also shown coupled with both the first or upper holder 222A and the second or lower holder 222B (e.g., based on connection with the third or upper right linkage 224C and the fourth or lower right linkage 224D).

In use, the foldable biasing members 220 can facilitate reconfiguration between the collapsed state (e.g., FIG. 20) and the expanded state (e.g., FIG. 21). For example, in the collapsed state (e.g., FIG. 20), the foldable biasing member 220 may be in a folded state (e.g., approximating a curve or arc). In the folded state, the foldable biasing member 220 may be arranged so that opposite ends (e.g., the first end 230 and the second end 232) are aligned (e.g., positioned underneath or over one another). In the collapsed state (e.g., FIG. 20), the foldable biasing members 220 from opposite sides of the device 101 may form loops that overlap one another, while in the expanded state (e.g., FIG. 21) the foldable biasing members 220 from opposite sides of the device 101 may be spaced apart from each other without overlap. Also in the collapsed state (e.g., FIG. 20), the holder 222 may be arranged at least partially within the channel 234 of the linkage 224.

Upon release from constraint, the foldable biasing member 220 may expand outwardly, e.g., at least partially straightening to move away from the folded state (e.g., moving from the state shown in FIG. 20 to that shown in FIG. 21). In response to the outward expansion, linkages 224 that were facing, adjacent, or aligned with one another may be moved apart from one another (e.g., as may be appreciated in FIG. 21 with the first linkage 224A and the second linkage 224B that are displaced apart from each other away from the starting position shown in FIG. 20).

Also in response to the outward expansion, rotation may occur relative to the hinge 225 (e.g., about the post 226 and seat 228). Rotation about the hinge 225 may re-orient the linkage 224A so that the channel 234 at least partially moves away from the carrier 118 and exposes the microneedles 116. Also in response to the outward expansion, the microneedles 116 may be moved outward for engagement with surrounding tissue.

Additional features may be included to control and/or constrain deployment. As one example that may be best seen in FIG. 22, the holder 222 can include a releasable attachment surface 238. The releasable attachment surface 238 can be on an underside of the holder 222 and/or opposite the support surface 236. For example, the releasable attachment surface 238 is depicted in FIG. 22 as arranged on an underside of a projecting stem that extends away from the support surface 236. As may be best seen in FIG. 21, in use, releasable attachment surfaces 238A and 238B of opposing holders 222A and 222B may face one another in spaced apart relation in the expanded state. In contrast, as may best be seen in FIG. 20, in the collapsed state, releasable attachment surfaces 238A and 238B of opposing holders 222A and 222B may contact and/or engage one another. For example, the releasable attachment surfaces 238A and 238B may be releasably attached by a degradable adhesive or other feature capable of releasing in response to conditions encountered within the lumen 102. Engagement of the opposing releasable attachment surfaces 238A and 238B can retain the opposing holders 222A and 222B in alignment relative to one another and prevent either side (e.g., the left side or the right side in FIG. 20) from expanding before the other during reconfiguration from the collapsed state to the expanded state. For example, releasing the opposing releasable attachment surfaces 238A and 238B (e.g., in response to conditions in the lumen 102) can allow the middles of the opposing holders 222A and 222B to move apart from one another for deployment and allow the opposing holders 222A and 222B to remain in a symmetric or parallel orientation during deployment. Such a symmetric or parallel orientation may facilitate effective engagement by the entirety or a substantial portion of the microneedles 116 on a carrier 118, and may avoid an angled deployment that may only dispose a select few microneedles 116 at an end of the holder 222 in a suitable position for engagement with surrounding tissue. In addition or as an alternative, the opposing holders 222A and 222B may be retained in a parallel orientation prior to deployment by a releasable collar or clamp around an exterior of the assembly in addition to or in lieu of the releasable attachment surfaces 238 on an interior of the assembly.

In some examples, deployment may be controlled and/or constrained by a hinge stopper 240. For example, as may best be seen in FIG. 22, the hinge stopper 240 may include a hinge stopping surface 242 on the holder 222 and/or a hinge-stopping surface 244 on the linkage 224. The hinge stopping surface 242 on the holder 222 and/or the hinge-stopping surface 244 on the linkage 224 may be arranged to contact or obstruct each other and/or other parts during relative rotation in deployment. In use, the hinge stopper may prevent over-rotation of the holder 222 beyond a predetermined limit relative to the linkage 224 and/or the foldable biasing member 220. Preventing over-rotation may prevent over-extension, inversion, and/or other misalignment or uneven actuation of the microneedles 116 in deployment. As an illustrative example, the hinge stopper 240 may prevent rotation past an angle of 80° between the holder 222 and the linkage 224, although 60°, 65°, 70°, 75°, 80°, 85°, 90°, 95°, 100°, or other maximum angles may be utilized.

In use, the foldable biasing member 220 may provide a central and substantial through-passage and/or bypass passage in the expanded state (e.g., between or around the foldable biasing members 220) and thus prevent or avoid full obstruction or occlusion of the lumen of the duodenum or other relevant body lumen 102. Additionally, the foldable biasing member 220 may provide substantially straight outward movement of the microneedles 116 so as to engage perpendicular to the lining of the lumen wall 103 of the body lumen 102 and reduce or avoid shearing forces that might occur if the mechanical actuator 120 instead imparted some tangentially-oriented components in addition to straight outward components (such as those oriented along a radial or normal direction, which may correspond to a direction perpendicular to the long axis of the lumen 102).

Figure 25:
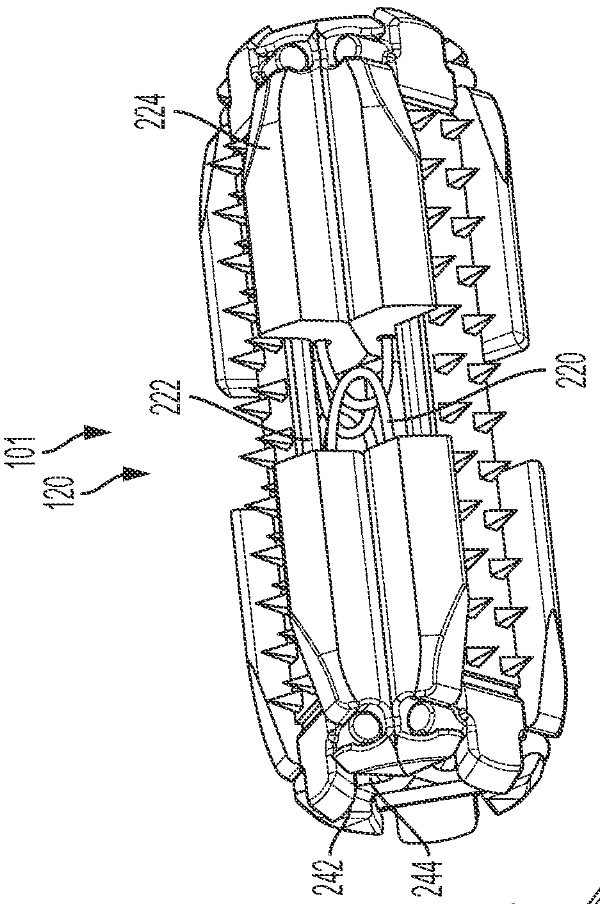
FIG. 25 shows a perspective view of a collapsed, ready state of the actuator of FIG. 24 according to certain examples of the present disclosure.
Figure 24:
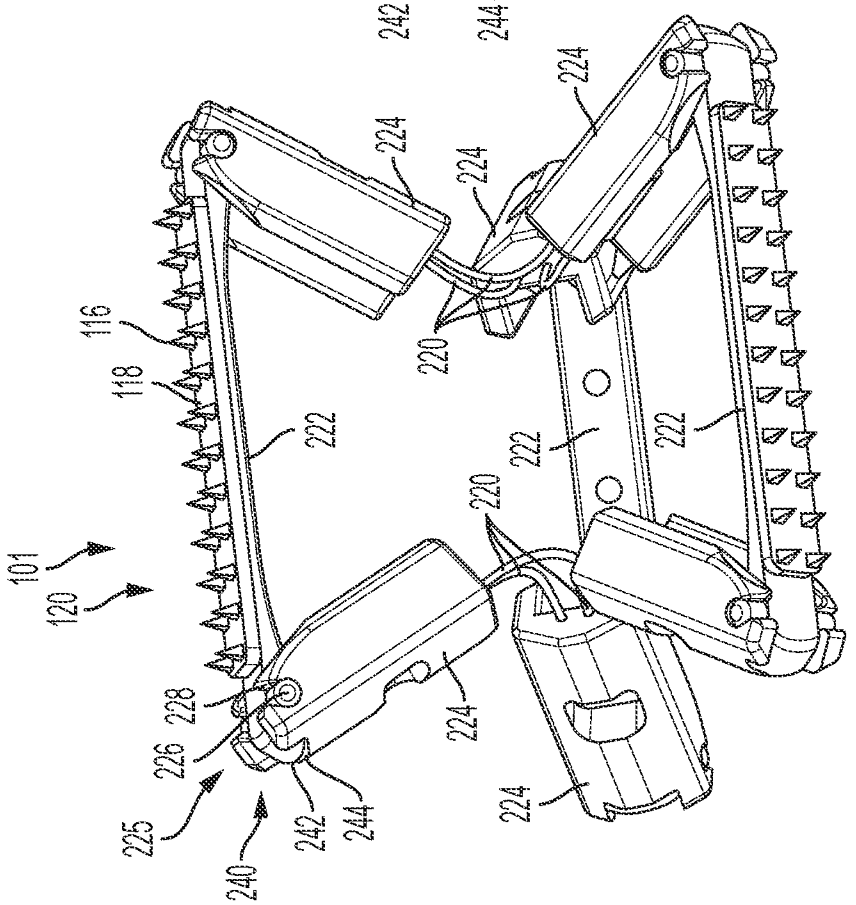
FIG. 24 shows a perspective view of an expanded, deployed state of an actuator with additional foldable biasing members according to certain examples of the present disclosure.

FIG. 24 is a perspective view showing further examples of structure that may be incorporated into the system 100. FIG. 24 depicts another example in which the mechanical actuator 120 may include a foldable biasing member 220. Various features in FIG. 24 may correspond to features described above with respect to FIGS. 20-23, and for simplicity, description of such features will not be repeated. Where FIG. 24 shows a perspective view of the foldable biasing member 220 in an expanded, deployed state, FIG. 25 shows a perspective view of a corresponding ready, collapsed state.

FIG. 24 illustrates an example in which more than two holders 222 are utilized. For example, in FIG. 24, three holders 222 are included. Each holder 222 is depicted as hingedly attached at opposite sides or ends. For example, each holder 222 is shown arranged in engagement with a pair of respective linkages 224. Three linkages 224 are shown at each end of the device 101 for a total of six linkages 224. In contrast to the arrangement in FIG. 21 that includes two foldable biasing members 220 that both extend from one linkage 224 and are both received in a single other linkage 224, the arrangement in FIG. 24 includes foldable biasing members 220 that extend from one linkage 224 to multiple other linkages 224. The foldable biasing members 220 may extend from a single linkage 224 to multiple laterally adjacent linkages 224. For example, on the right-hand side in FIG. 24, one foldable biasing member 220 extends from the top linkage 224 to the leftward linkage 224 that is arranged laterally adjacent in the counterclockwise direction, while another foldable biasing member 220 extends from the top linkage 224 to the rightward linkage 224 that is arranged laterally adjacent in the clockwise direction.

FIG. 24 illustrates an example in which the hinge 225 is provided in a different form factor from that shown in FIGS. 20-23. For example, the hinge 225 in FIG. 24 includes a post 226 borne by the holder 222 and a seat 228 borne by the linkage 224, although other arrangements may be utilized other hinging interface options described herein.

FIG. 24 further illustrates an example in which hinge stopper 240 is provided in a different form factor from that shown in FIGS. 20-23. For example, the hinge stopper 240 in FIG. 24 on the holder 222 includes one hinge stopping surface 242 formed as a flange or extension arranged to engage another hinge-stopping surface 244 on the linkage 224 during rotation in deployment and to prevent or mitigate against over-rotation.

Figure 27:
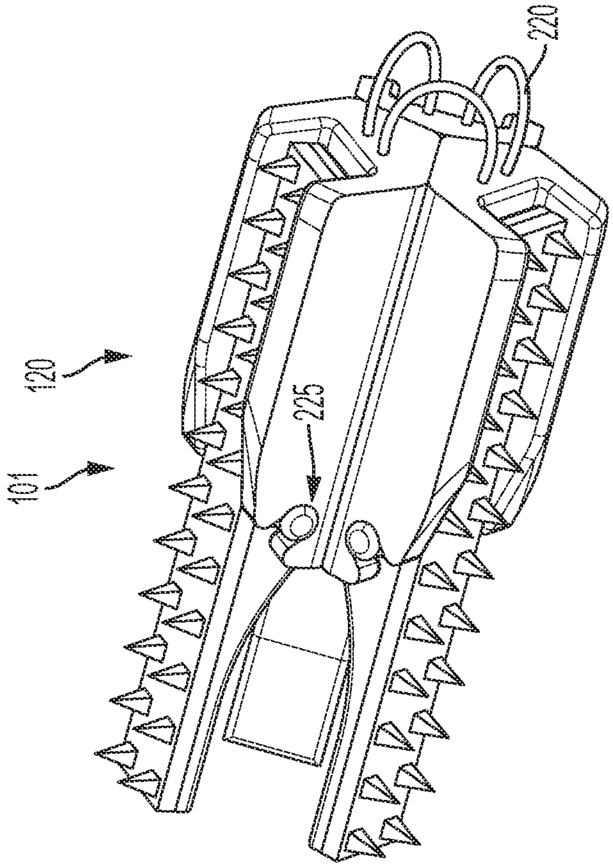
FIG. 27 shows a perspective view of a collapsed, ready state of the actuator of FIG. 26 according to certain examples of the present disclosure.
Figure 26:
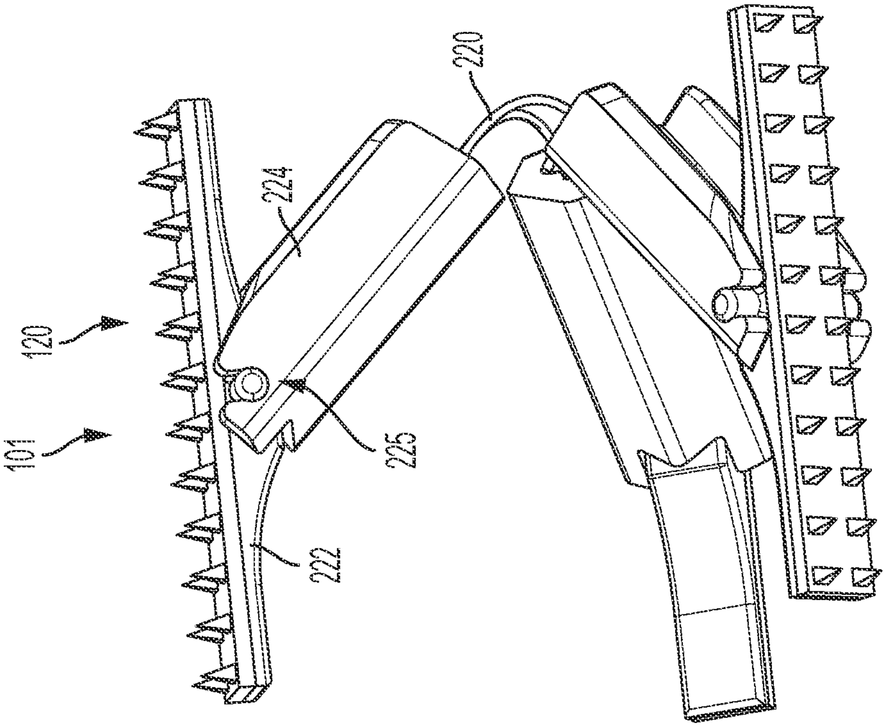
FIG. 26 shows a perspective view of an expanded, deployed state of an actuator with holders attached by central hinges according to certain examples of the present disclosure.

FIG. 26 is a perspective view showing further examples of structure that may be incorporated into the system 100. FIG. 26 depicts another example in which the mechanical actuator 120 may include a foldable biasing member 220. Various features in FIG. 26 may correspond to features described above with respect to FIGS. 20-23 and/or 24-25, and for simplicity, description of such features will not be repeated. Where FIG. 26 shows a perspective view of the foldable biasing member 220 in an expanded, deployed state, FIG. 27 shows a perspective view of a corresponding ready, collapsed state.

FIG. 26 illustrates an example in which the hinge 225 is coupled with a middle portion of the holder 222. For example, a single hinge 225 may couple the holder 222 to a remainder of the device 101, e.g., in contrast to the arrangements in FIGS. 20-23 and/or 24-25 in which holders 222 are engaged with multiple hinges 225 at opposite ends or sides. Coupling a holder 222 via single hinge may provide degrees of freedom for a holder 222 to continue rotating during deployment, e.g., so that if one end engages surrounding tissue, the opposite end can continue rotating to engage surrounding tissue too.

Figure 28:
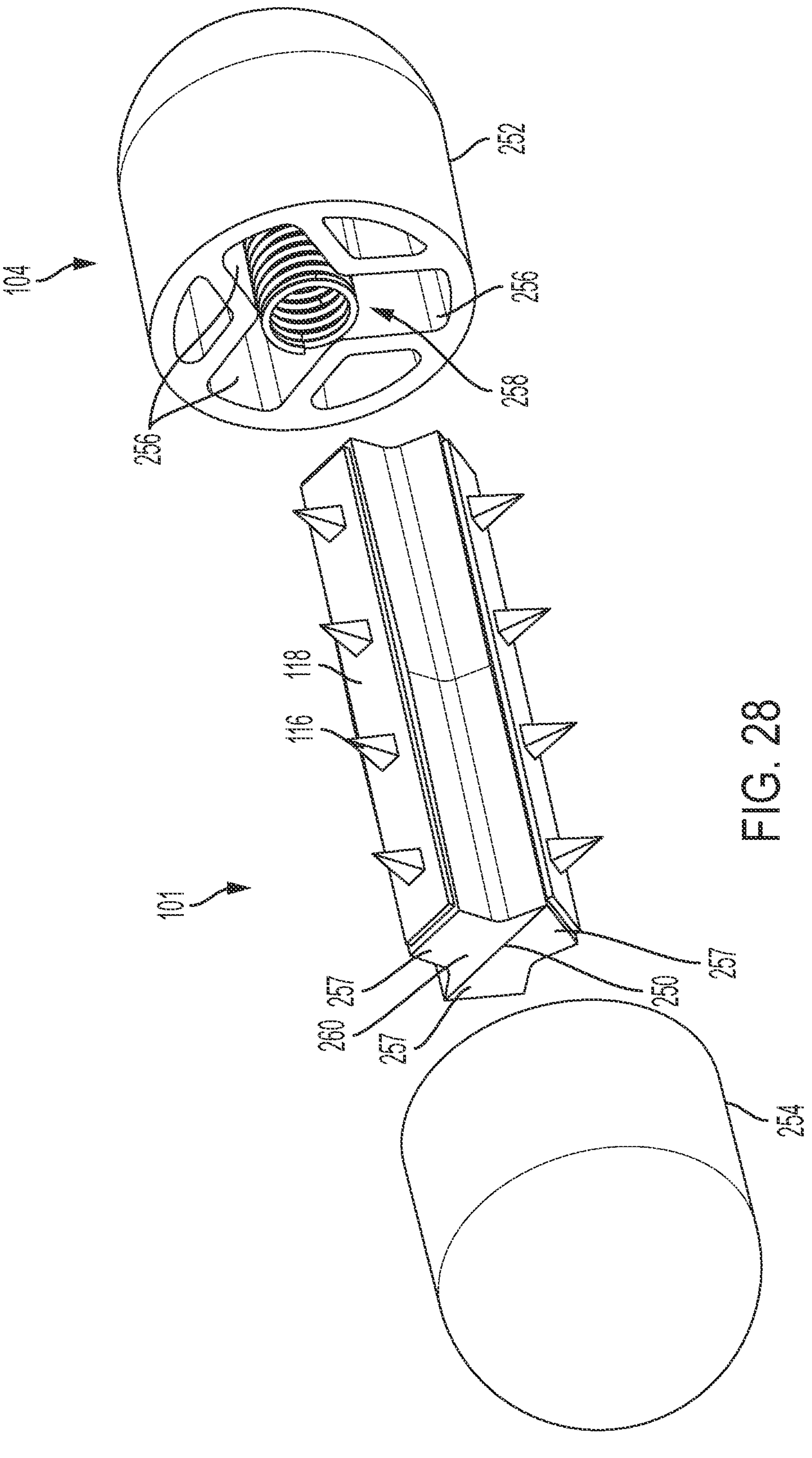
FIG. 28 shows an exploded assembly view of an actuator with capsule shell portions deployable relative to a core according to certain examples of the present disclosure.

FIG. 28 is a perspective view showing further examples of structure that may be incorporated into the system 100 (e.g., in lieu of and/or along with other features herein). The device 101 can include a core 250. The core 250 may be capable of deploying from the capsule 104 in use.

Microneedles 116 are depicted as supported by carriers 118 that are separately mounted to the core 250, although other arrangements are possible, including, but not limited to arrangements in which the microneedles 116 and/or carriers 118 are instead integrally formed.

The capsule 104 can include features to facilitate receipt of the core 250 within the capsule 104. For example, the capsule may include a first shell portion 252 and a second shell portion 254 that may be combined to form the capsule 104 in use. The capsule 104 can include matching profiles or geometries relative to the core 250. For example, the capsule 104 in FIG. 28 is shown with three grooves 256 respectively sized to receive three flanges 257 defined by the core 250, although other numbers and/or sizing may be utilized. The flanges 257 may provide attachment surfaces for the microneedles 116, for example. The grooves 256 may provide indexing and/or otherwise prevent or limit rotation or other movement of the core 250 within the capsule 104 in use. The grooves 256 may be sized to accommodate the microneedles 116, such as by providing a space in which the microneedles 116 may be arranged without contacting other portions of the capsule 104 in a manner that could otherwise lead to dulling of the microneedles prior to use.

The device 101 can include a launcher 258. The launcher 258 is depicted as springs in FIG. 28 but may correspond to any structure capable of separating the first shell portion 252 and the second shell portion 254 from each other and/or from the core 250 in use. Other non-limiting examples may include expandable material (such as super absorbable polymer) and/or utilization of propellant or other gas expansion. The launcher 258 may be attached and/or otherwise retained within the first shell portion 252 and/or the second shell portion 254 and allow the core 250 to be independent or separate from the launcher 258. In some embodiments, some portion of the launcher 258 may additionally or alternatively be retained within or otherwise coupled with the core 250 and/or may otherwise be capable of separating from the first shell portion 252 and/or the second shell portion 254.

Figure 29:
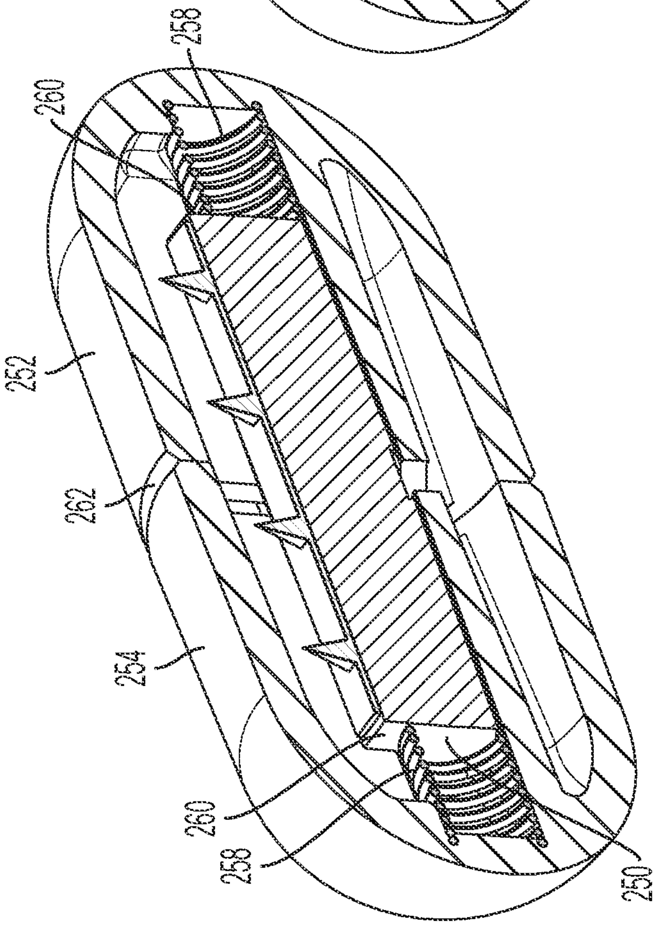
FIG. 29 shows an assembled view of an actuator with leverage surfaces on an exterior of the core according to certain examples of the present disclosure.

The launcher 258 may interact with and/or respond to other suitable structures. As one example, the core 250 may include at least one leverage surface 260. For example, in FIG. 29, leverage surfaces 260 are arranged on either end on an exterior of the core 250 and provide surfaces against which the launcher 258 can press in use. In FIG. 29, the launcher 258 is arranged entirely outside of the core 250.

In some examples, relevant structure may be at least partially within the core 250. For example, in FIG. 29, the core 250 includes an internal hollow cavity terminating at leverage surfaces 260. Springs or other structure of the launcher 258 can be positioned extending at least partially inside the core 250, e.g., to press against leverage surfaces 260 in use. In some examples, the core 250 may be fully hollow and may allow components of the launcher 258 to abut, contact, or otherwise engage each other through the core 250.

In use, the first shell portion 252 and the second shell portion 254 may be releasably attached together by a joint 262 (e.g., FIG. 29). The joint 262 may extend around a perimeter of the capsule 104, for example. The joint 262 may correspond to a coating or other suitable structure that may degrade or otherwise cause release in response to stimuli or conditions in or en route to the duodenum or other target location, such as in response to a chemical (such as pH), electrical, mechanical, or external stimulus (such as ultrasound energy that may be applied to affect particular compositions). Prior to degradation or release, the joint 262 may provide sufficient strength to retain the first shell portion 252 and the second shell portion 254 in engagement with each other notwithstanding the presence of the launcher 258.

Figure 30:
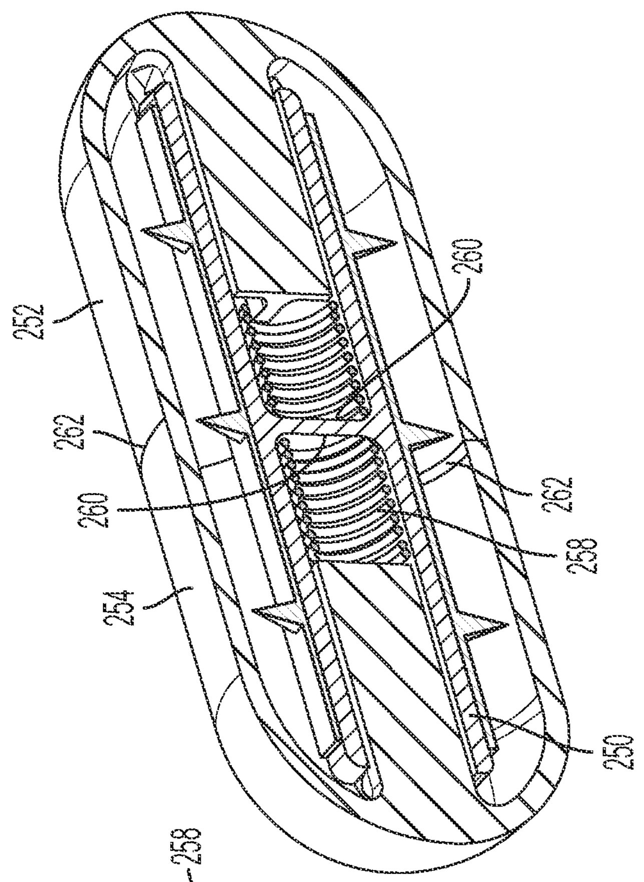
FIG. 30 shows an assembled view of an actuator with leverage surfaces on an interior of the core according to certain examples of the present disclosure.

The launcher 258 may be operable or activated upon overcoming or escaping from constraint provided by the joint 262. For example, in use, the capsule 104 may reach the duodenum or other target location and begin to degrade and/or release. This may prompt the launcher 258 to drive the first shell portion 252 and the second shell portion 254 way from each other and/or the core 250 (e.g., shifting from a stowed state shown in either FIG. 29 or FIG. 30 to a deployed state shown in FIG. 28). In an example in which the launcher 258 includes springs, the springs may push against the leverage surfaces 260 for driving the first shell portion 252 and the second shell portion 254 away. In an example in which the launcher 258 includes expandable material, fluid from the target location may enter and cause a chemical reaction to cause expansion for driving the first shell portion 252 and the second shell portion 254 away, for example.

Figure 31:
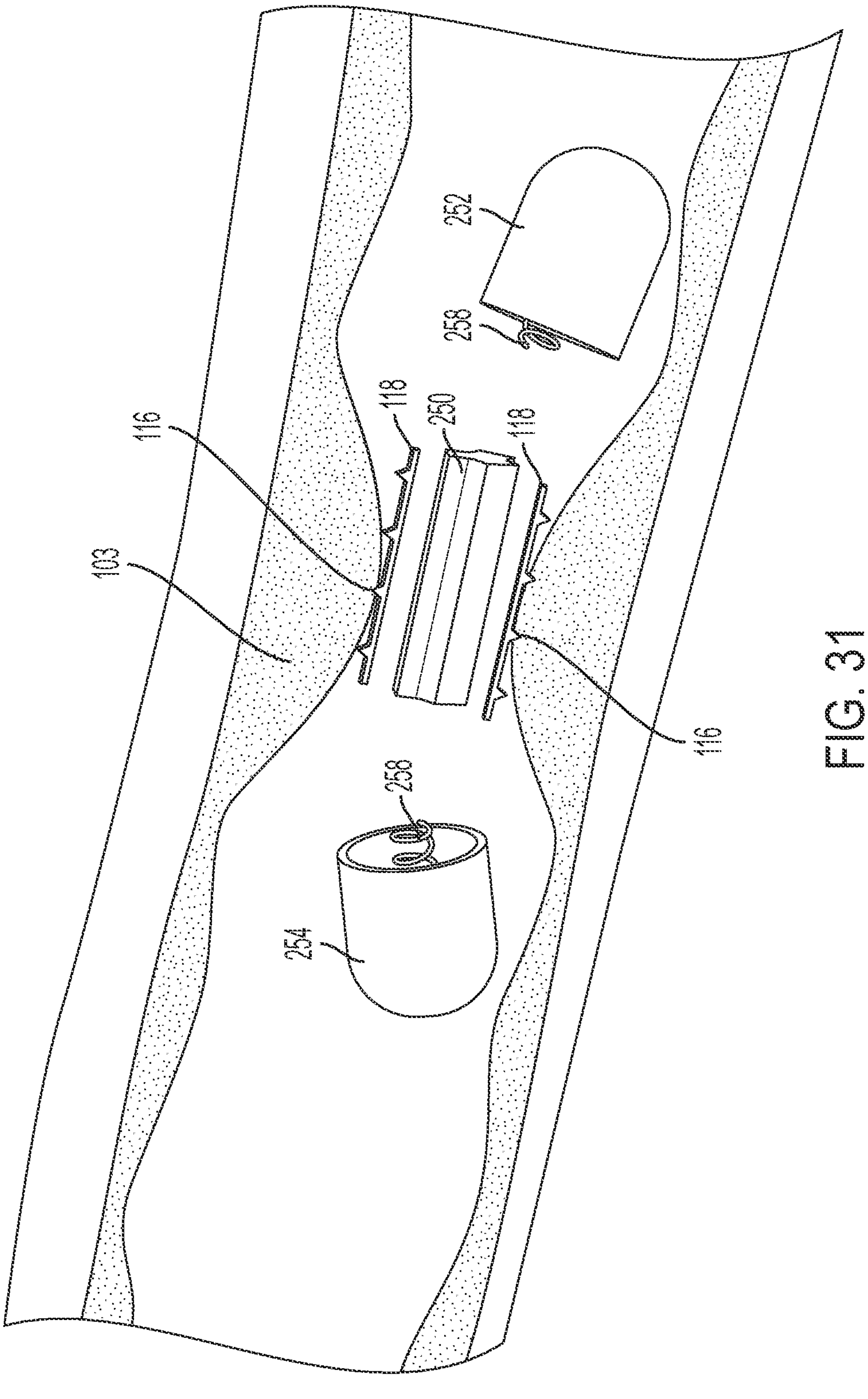
FIG. 31 shows the actuator of FIG. 28 in an environment in use according to certain examples of the present disclosure.

The launcher 258 driving the first shell portion 252 and the second shell portion 254 away may expose the microneedles 116 in a suitable position for penetrating surrounding tissue. For example, referring to FIG. 31, the tissue of lumen wall 103 of the duodenum or other target location may contract around the core 250, such as in response to peristaltic contractions. Such contraction around the core 250 may provide sufficient force to achieve penetrating engagement of the microneedles 116 into the lining of the duodenum or other target location. Penetrating engagement may cause the microneedles 116 to remain in engagement with the tissue absent a suitable removal force. In various examples, the carriers 118 of microneedles 116 may be attached to the core 250 with adhesive or other types of bonding that is configured to release when subjected to a release force less than the removal force magnitude. As a result, the carriers 118 of microneedles 116 may separate from the core 250 and remain engaged in the tissue as the tissue retracts during peristaltic or other cycles. Remaining engaged in the tissue may facilitate delivery of payload via the microneedles 116, for example. The removal force may vary according to arrangement of microneedles 116 implemented, and the release force may be adjusted based on the bonding technique utilized.

The core 250, the launcher 258, and/or other associated components may be formed of suitable material. In some examples, at least some of the material is a flexibly resilient material (such as having sufficient flexibility to allow the launcher 258 to compress, and further having sufficient resiliency to bias the material toward expanding, e.g., to drive the first shell portion 252 and the second shell portion 254 away). In some examples, material is biodegradable material (e.g., capable of degrading within a gastrointestinal tract) and/or suitable for construction by 3D-printing or other specific fabrication techniques. Some examples of suitable materials can include SLA, 3D-printed durable resin, gelatin paper or sheets, rice paper or sheets, polylactic acid, nylon, polyester, PVA (polyvinyl alcohol), or corn-based polymers. In some examples, the material used may include non-biodegradable material (e.g., which may be passed via excretion). As non-limiting examples, materials may include stainless steel or other metals (such as for coil springs or other spring members for the launcher 258), plastics (such as for the core 250, the first shell portion 252, and/or the second shell portion 254), or other substances.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure. For example, more or fewer steps of the processes described herein may be performed according to the present disclosure. Moreover, other structures may perform one or more steps of the processes described herein.

In some aspects, a device, a system, or a method is provided according to one or more of the following Aspects or according to some combination of the elements thereof. In some aspects, a device or a system described in one or more of these Aspects can be utilized to perform a method described in one of the other Aspects. Further, features described with respect to a device or a system may be implemented relative to a method or vice versa.

Aspect 1. A device comprising a capsule containing an array of microneedles and a mechanical actuator, wherein the device is in an ingestible form for delivery to a duodenum of a subject and releases the mechanical actuator from constraint by the capsule in response to stimuli or conditions in or en route to the duodenum, wherein the mechanical actuator upon release from constraint by the capsule expands outwardly in a direction away from a central longitudinal axis of the mechanical actuator and drives the array of microneedles into penetrating engagement with a lining of the duodenum, and wherein the penetrating engagement facilitates delivery of a payload via the microneedles.

Aspect 1A. The device of aspect 1, wherein the mechanical actuator comprises:

a foldable biasing member comprising a first end and a second end, the foldable biasing member exhibiting a flexibility permitting the first end and the second end to be foldable toward one another for movement from an expanded state toward a collapsed state, the biasing member exhibiting a resilience to urge the first end and the second end apart from one another for movement from the collapsed state toward the expanded state; and a holder hingedly attached with the first end of the biasing member and comprising a support surface for supporting the array of microneedles.

Aspect 2. The device of aspect 1, wherein the device is entirely formed of one or more biodegradable materials, whereby the device is fully biodegradable instead of leaving some portion that requires passing via excretion to be eliminated from the subject.

Aspect 3. The device of aspect 1, wherein the mechanical actuator is formed of a structure that allows passage therethrough so as to avoid full obstruction of a lumen of the duodenum by the mechanical actuator in an outwardly expanded state of the mechanical actuator.

Aspect 4. The device of aspect 1, wherein the mechanical actuator comprises:

a collapsible tube compressible toward and expandable away from the central longitudinal axis of the mechanical actuator;

an upper crossbeam and a lower crossbeam joined by lateral columns having middle hinges;

a coil having a number of overlapping turns that are more tightly wound in the collapsed state than in the expanded state;

a plurality of curved arms attached at proximal ends to a central core and movable so distal ends rotate away from the core in a spiraling direction to move from the collapsed state to the expanded state; or a hub coupled with a plurality of double-hinged arms each comprising (i) a first hinge coupling a proximal portion of the arm to the hub and (ii) a second hinge coupling the proximal portion of the arm to a distal portion of the arm.

Aspect 5. The device of aspect 1, wherein the array of microneedles is borne by an expandable band arranged around the mechanical actuator and configured to expand in response to expansion of the mechanical actuator.

Aspect 6. A system comprising:

a capsule comprising a shell having:

an inner surface defining an interior volume of the capsule; and an outer surface sized to pass through a lumen defined by a lining of a gastrointestinal tract;

a carrier sized to fit within the interior volume of the capsule and bearing an array of microneedles; and a mechanical actuator operable for moving the carrier outwardly to cause the microneedles to penetrate the lining of the gastrointestinal tract, the mechanical actuator comprising a flexibly resilient material having a flexibility permitting collapsing of the mechanical actuator away from an expanded state and toward a collapsed state in which the mechanical actuator fits within the interior volume of the capsule, the flexibly resilient material further having a resiliency that biases the mechanical actuator toward expanding outwardly from the collapsed state toward the expanded state to move the carrier outwardly upon the mechanical actuator overcoming or escaping from constraint provided by the capsule.

Aspect 6A. The system of aspect 6, wherein the mechanical actuator comprises a biasing member comprising a first end and a second end foldable toward one another; and a holder hingedly attached with the first end of the biasing member and comprising a support surface for supporting the array of microneedles.

Aspect 7. The system of aspect 6, wherein the capsule is configured to release the mechanical actuator from constraint in a portion of the gastrointestinal tract corresponding to the duodenum.

Aspect 8. The system of aspect 7, wherein the capsule is configured to degrade in the duodenum to release the mechanical actuator from constraint.

Aspect 9. The system of aspect 6, wherein the mechanical actuator and the carrier are each configured to move outwardly in a direction away from a central longitudinal axis of the mechanical actuator.

Aspect 10. The system of aspect 6, wherein the mechanical actuator comprises a collapsible tube compressible toward and expandable away from the central longitudinal axis of the mechanical actuator.

Aspect 11. The system of aspect 10, wherein the collapsible tube is formed of a network of interconnected flexible members in which spacing between the members is greater in the expanded state than in the collapsed state.

Aspect 12. The system of aspect 6, wherein the mechanical actuator comprises an upper crossbeam and a lower crossbeam joined by lateral columns having middle hinges.

Aspect 13. The system of aspect 12, wherein at least one of the middle hinges when shifting between the collapsed state and the expanded state moves from underneath one end of the upper crossbeam to underneath an opposite end.

Aspect 14. The system of aspect 12, wherein the middle hinges pass by one another when shifting between the collapsed state and the expanded state.

Aspect 15. The system of aspect 12, wherein the lateral columns comprise at least one set of two columns that define a slot therebetween through which at least one other of the lateral column travels during shifting between the collapsed and the expanded state.

Aspect 16. The system of aspect 6, wherein the mechanical actuator comprises a coil having a number of overlapping turns that are more tightly wound in the collapsed state than in the expanded state.

Aspect 17. The system of aspect 6, wherein the mechanical actuator comprises a plurality of curved arms attached at proximal ends to a central core and movable so distal ends rotate away from the core in a spiraling direction to move from the collapsed state to the expanded state.

Aspect 18. The system of aspect 6, wherein the mechanical actuator comprises a hub coupled with a plurality of double-hinged arms each comprising (i) a first hinge coupling a proximal portion of the double-hinged arm to the hub and (ii) a second hinge coupling the proximal portion of the double-hinged arm to a distal portion of the double-hinged arm.

Aspect 19. The system of aspect 18, wherein in the collapsed state, the proximal portion of the double-hinged arm is located outwardly of the distal portion of the double-hinged arm relative to a central longitudinal axis of the mechanical actuator.

Aspect 20. The system of aspect 18, wherein in moving from the collapsed state to the expanded state, (i) the proximal portion of the double-hinged arm opens away from the hub, and (ii) the distal portion of the double-hinged arm opens away from the proximal portion of the double-hinged arm.

Aspect 21. The system of aspect 6, wherein the carrier comprises an expandable band arranged around the mechanical actuator.

Aspect 22. The system of aspect 6, wherein the array of microneedles is mechanically coupled with the mechanical actuator.

Aspect 23. The system of aspect 22, wherein the array of microneedles is integrally formed into a material of the mechanical actuator.

Aspect 24. The system of aspect 6, wherein the array of microneedles comprises characteristics that include:

an aspect ratio of greater than or equal to 2 and less than or equal to 3;

a pitch of greater than or equal to 1.5 mm and less than or equal to 2 mm; and a sharpness of less than 1 micron.

Aspect 25. A method of treating a subject with a drug or biotherapeutic agent, the method comprising administering to the subject the device of aspect 1, wherein the device comprises a drug or biotherapeutic payload.

Aspect 26. A method of treating a subject with a drug or biotherapeutic agent, the method comprising administering to the subject the system of aspect 6, wherein the system comprises a drug or biotherapeutic payload.

Aspect 27. A method of fabrication comprising:

forming an assembly by coupling an array of microneedles with a mechanical actuator expandable in an outward direction from a central longitudinal axis; and disposing the assembly within a capsule having a first state in which the capsule constrains the mechanical actuator from expanding, the capsule reconfigurable in a target location within a subject to a second state in which constraint by the capsule is eliminated to permit the mechanical actuator to expand for driving the array of microneedles into engagement with tissue at the target location.

Aspect 28. The method of aspect 27, further comprising forming the array of microneedles prior to coupling with the mechanical actuator.

Aspect 29. The method of aspect 27, wherein coupling the array of microneedles with the mechanical actuator comprises integrally forming the array of microneedles into material of the mechanical actuator.

Aspect 30. The method of aspect 27, wherein coupling the array of microneedles with the mechanical actuator comprises disposing the mechanical actuator within an expandable band that bears the microneedles.

Aspect 31. The method of aspect 27, further comprising forming the array of microneedles with characteristics that include:

an aspect ratio of greater than or equal to 2 and less than or equal to 3;

a pitch of greater than or equal to 1.5 mm and less than or equal to 2 mm; or a sharpness of less than 1 micron.

In some aspects, a device, a system, or a method is provided according to one or more of the following Examples or according to some combination of the elements thereof. In some aspects, a device or a system described in one or more of these Examples can be utilized to perform a method described in one of the other Examples. Further, features described with respect to a device or a system may be implemented relative to a method or vice versa.

Example 1

A system comprising:

a capsule comprising a shell having:

an inner surface defining an interior volume of the capsule; and an outer surface sized to pass through a lumen defined by a lining of a gastrointestinal tract;

a carrier sized to fit within the interior volume of the capsule and bearing an array of microneedles; and a mechanical actuator operable for moving the carrier outwardly to cause the microneedles to penetrate the lining of the gastrointestinal tract, the mechanical actuator comprising:

- a foldable biasing member comprising a first end and a second end, the foldable biasing member comprising a flexibly resilient material having a flexibility permitting the first end and the second end to be foldable toward one another for movement from an expanded state toward a collapsed state in which the mechanical actuator fits within the interior volume of the capsule, the flexibly resilient material further having a resiliency that biases the first end and the second end apart from one another for movement from the collapsed state toward the expanded state to move the carrier outwardly upon the mechanical actuator overcoming or escaping from constraint provided by the capsule; and
- a holder hingedly attached with the first end of the biasing member and comprising a support surface for supporting the carrier bearing the array of microneedles.

Example 2

The system of Example 1, further comprising a linkage coupled with the first end of the folding biasing member.

Example 3

The system of Example 2, wherein the linkage comprises a channel in which the holder is received in the collapsed state to space apart tips of the array of microneedles from the inner surface of the capsule.

Example 4

The system of Example 2, wherein the holder is hingedly attached with the first end of the biasing member via a hinge included at least in part on the linkage.

Example 5

The system of Example 4, further comprising a hinge stopping surface included on the holder or the linkage and arranged to prevent rotation of the hinge past a predetermined limit.

Example 6

The system of Example 1, wherein the foldable biasing member comprises a nitinol wire.

Example 7

The system of Example 1, wherein the foldable biasing member is a first foldable biasing member, and wherein the holder is hingedly attached at opposite sides to the first foldable biasing member and a second foldable biasing member.

Example 8

The system of Example 1, wherein the foldable biasing member and the holder are included in an assembly comprising:

a first holder and a second holder;

a first linkage, a second linkage, a third linkage, and a fourth linkage; and a first foldable biasing member and a second first foldable biasing member arranged such that:

the first foldable biasing member has opposite ends received respectively in the first linkage and the second linkage;

the second foldable biasing member has opposite ends received respectively in the third and fourth linkages;

the first holder is hingedly coupled at opposite sides to the first linkage and the third linkage; and the second holder is hingedly coupled at opposite sides to the second linkage and the fourth linkage.

Example 9

The system of Example 1, wherein the holder is a first holder that comprises a releasable attachments surface arranged to attach to a second holder in the collapsed state and configured to release to permit symmetric deployment of first holder and the second holder relative to one another.

Example 10

The system of Example 1, comprising at least three holders interconnected by at least three foldable biasing members arranged to respectively extend between laterally adjacent holders.

Example 11

A system comprising:

a capsule comprising a shell having:

a first shell portion;

a second shell portion;

a joint releasably attaching the first shell portion with the second shell portion;

an inner surface defined at least in part by the first shell portion and the second shell portion and defining an interior volume of the capsule; and an outer surface defined at least in part by the first shell portion and the second shell portion and sized to pass through a lumen defined by a lining of a gastrointestinal tract;

a carrier sized to fit within the interior volume of the capsule and bearing an array of microneedles; and a launcher operable upon overcoming or escaping from constraint provided by the joint and operable for driving the first shell portion and the second shell portion away from the carrier to expose the array of microneedles.

Example 11A

The system of Example 11, wherein the launcher is operable to expose the array of microneedles in a position for achieving penetrating engagement with the lining of the gastrointestinal tract caused by peristaltic contraction of the gastrointestinal tract about the array of microneedles.

Example 12

The system of Example 11, wherein portions of the launcher are respectively attached in the first shell portion and the second shell portion so as to be retained therein after the driving away of the first shell portion and the second shell portion from the carrier.

Example 13

The system of Example 11, wherein the launcher comprises a coil spring arranged to push against a leverage surface of a core coupled with the carrier.

Example 14

The system of Example 11, wherein the first shell portion and the second shell portion include grooves shaped to receive flanges extending from a core coupled with the carrier so as to limit movement of the core within the capsule.

Example 15

The system of Example 11, wherein the carrier is attached to a core by a bond releasable in response to a release force that is smaller in magnitude than a removal force sufficient to remove the array of microneedles from penetrating engagement with the lining of the gastrointestinal tract.

Example 16

A system comprising a mechanical actuator configured for microneedle delivery, the mechanical actuator comprising:

a foldable biasing member comprising a first end and a second end, the foldable biasing member comprising a flexibly resilient material having a flexibility permitting the first end and the second end to be foldable toward one another for movement from an expanded state toward a collapsed state in which the mechanical actuator fits within a volume sized to fit within an ingestible capsule, the flexibly resilient material further having a resiliency that biases the first end and the second end apart from one another for movement from the collapsed state toward the expanded state; and a holder hingedly attached with the first end of the biasing member and comprising a support surface configured for supporting a carrier bearing an array of microneedles, the support surface configured for supporting the carrier for outward movement for deployment of the microneedles in response to movement from the collapsed state toward the expanded state.

Example 17

The system of Example 16, further comprising the carrier bearing the array of microneedles.

Example 18

The system of Example 16, further comprising the capsule.

Example 19

The system of Example 16, wherein the foldable biasing member and the holder are included in an assembly comprising:

a first holder and a second holder;

a first linkage, a second linkage, a third linkage, and a fourth linkage; and a first foldable biasing member and a second first foldable biasing member arranged such that:

the first foldable biasing member has opposite ends received respectively in the first linkage and the second linkage;

the second foldable biasing member has opposite ends received respectively in the third and fourth linkages;

the first holder is hingedly coupled at opposite sides to the first linkage and the third linkage; and the second holder is hingedly coupled at opposite sides to the second linkage and the fourth linkage.

Example 20

A device comprising a capsule containing an array of microneedles and a launcher, wherein the device is in an ingestible form for delivery to a duodenum of a subject and releases a first shell portion and a second shell portion of the capsule from one another in response to stimuli or conditions in or en route to the duodenum, wherein the launcher drives the released first shell portion and the second shell portion away from one another to expose the array of microneedles in a position for achieving penetrating engagement with a lining of the duodenum caused by peristaltic contraction of the lining of the duodenum about the exposed array of microneedles, and wherein the penetrating engagement facilitates delivery of a payload via the microneedles.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases “in one example,” “in an example,” “in one implementation,” or “in an implementation,” or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word “or” is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

That which is claimed is:

1. A system comprising:

a capsule comprising a shell having:

an inner surface defining an interior volume of the capsule; and an outer surface;

a carrier sized to fit within the interior volume of the capsule and bearing an array of microneedles; and a mechanical actuator operable for moving the carrier outwardly to cause the microneedles to engage tissue, the mechanical actuator comprising:

a foldable biasing member comprising a first end and a second end, the foldable biasing member including a foldable portion comprising a flexibly resilient material having a flexibility permitting the first end and the second end to be foldable toward one another for movement from an expanded state toward a collapsed state in which the mechanical actuator fits within the interior volume of the capsule, the flexibly resilient material further having a resiliency that biases the first end and the second end apart from one another for movement from the collapsed state toward the expanded state to move the carrier outwardly upon the mechanical actuator overcoming or escaping from constraint provided by the capsule; and a holder hingedly attached with the first end of the biasing member by a hinge distinct from the foldable portion of the biasing member such that the holder is pivotable about the hinge relative to the first end of the biasing member, the holder comprising a support surface for supporting the carrier bearing the array of microneedles.

2. The system of claim 1, further comprising a linkage coupled with the first end of the foldable biasing member.

3. The system of claim 2, wherein the linkage comprises a channel in which the holder is received in the collapsed state to space apart tips of the array of microneedles from the inner surface of the capsule.

4. The system of claim 2, wherein the holder is hingedly attached with the first end of the biasing member via the hinge, and wherein the hinge is included at least in part on the linkage.

5. The system of claim 4, further comprising a hinge stopping surface included on the holder or the linkage and arranged to prevent rotation of the hinge past a predetermined limit.

6. The system of claim 1, wherein the foldable biasing member comprises a nitinol wire.

7. The system of claim 1, wherein the foldable biasing member is a first foldable biasing member, and wherein the holder is hingedly attached at opposite sides to the first foldable biasing member and a second foldable biasing member.

8. The system of claim 1, wherein the foldable biasing member and the holder are included in an assembly comprising:

a first holder and a second holder;

a first linkage, a second linkage, a third linkage, and a fourth linkage; and a first foldable biasing member and a second foldable biasing member arranged such that:

the first foldable biasing member has opposite ends received respectively in the first linkage and the second linkage;

the second foldable biasing member has opposite ends received respectively in the third and fourth linkages;

the first holder is hingedly coupled at opposite sides to the first linkage and the third linkage; and the second holder is hingedly coupled at opposite sides to the second linkage and the fourth linkage.

9. The system of claim 1, wherein the holder is a first holder that comprises a releasable attachments surface arranged to attach to a second holder in the collapsed state and configured to release to permit symmetric deployment of the first holder and the second holder relative to one another.

10. The system of claim 1, comprising at least three holders interconnected by at least three foldable biasing members arranged to respectively extend between laterally adjacent holders.

11. The system of claim 1, wherein the outer surface of the capsule is sized to a target location within a subject.

12. The system of claim 1, wherein the outer surface of the capsule is sized to pass through a body lumen.

13. The system of claim 12, wherein the body lumen through which the outer surface is sized to pass is a gastrointestinal tract.

14. A system comprising a mechanical actuator configured for microneedle delivery, the mechanical actuator comprising:

a foldable biasing member comprising a first end and a second end, the foldable biasing member including a foldable portion comprising a flexibly resilient material having a flexibility permitting the first end and the second end to be foldable toward one another for movement from an expanded state toward a collapsed state in which the mechanical actuator fits within a volume sized to fit within a capsule, the flexibly resilient material further having a resiliency that biases the first end and the second end apart from one another for movement from the collapsed state toward the expanded state; and a holder hingedly attached with the first end of the biasing member by a hinge distinct from the foldable portion of the biasing member such that the holder is pivotable about the hinge relative to the first end of the biasing member, the holder comprising a support surface configured for supporting a carrier bearing an array of microneedles, the support surface configured for supporting the carrier for outward movement for deployment of the microneedles in response to movement from the collapsed state toward the expanded state.

15. The system of claim 14, further comprising the carrier bearing the array of microneedles.

16. The system of claim 14, further comprising the capsule.

17. The system of claim 14, wherein the foldable biasing member and the holder are included in an assembly comprising:

a first holder and a second holder;

a first linkage, a second linkage, a third linkage, and a fourth linkage; and a first foldable biasing member and a second foldable biasing member arranged such that:

the first foldable biasing member has opposite ends received respectively in the first linkage and the second linkage;

the second foldable biasing member has opposite ends received respectively in the third and fourth linkages;

the first holder is hingedly coupled at opposite sides to the first linkage and the third linkage; and the second holder is hingedly coupled at opposite sides to the second linkage and the fourth linkage.

18. The system of claim 14, wherein the capsule is an ingestible capsule.

* * * * *